US012629123B2

(12) United States Patent
Saeed et al.

(10) Patent No.: US 12,629,123 B2
(45) Date of Patent: May 19, 2026

(54) DEEP LEARNING APPARATUS AND METHOD FOR SEGMENTATION AND SURVIVAL PREDICTION FOR HEAD AND NECK TUMORS

(71) Applicant: Mohamed bin Zayed University of Artificial Intelligence, Abu Dhabi (AE)

(72) Inventors: Numan Saeed, Abu Dhabi (AE);
Ikboljon Sobirov, Abu Dhabi (AE);
Roba Majzoub, Abu Dhabi (AE);
Mohammad Yaqub, Abu Dhabi (AE)

(73) Assignee: Mohamed bin Zayed University of Artificial Intelligence, Abu Dhabi (AE)

( * ) Notice: Subject to any disclaimer, the term of this patent is extended or adjusted under 35 U.S.C. 154(b) by 828 days.

(21) Appl. No.: 17/849,943

(22) Filed: Jun. 27, 2022

(65) Prior Publication Data

US 2023/0414189 A1 Dec. 28, 2023

(51) Int. Cl.
| | |
|---|---|
| *G16H 10/60* | (2018.01) |
| *A61B 6/00* | (2006.01) |
| *A61B 6/50* | (2024.01) |
| *G06T 7/00* | (2017.01) |
| *G16H 50/20* | (2018.01) |

(52) U.S. Cl.
CPC ............ *A61B 6/5217* (2013.01); *A61B 6/501* (2013.01); *A61B 6/5235* (2013.01); *G06T 7/0012* (2013.01); *G16H 10/60* (2018.01); *G16H 50/20* (2018.01); *G06T 2207/10081* (2013.01); *G06T 2207/10104* (2013.01); *G06T 2207/20084* (2013.01); *G06T 2207/20221* (2013.01); *G06T 2207/30096* (2013.01)

(58) Field of Classification Search
CPC .............................. G16H 10/60; G16H 50/20
See application file for complete search history.

(56) References Cited

U.S. PATENT DOCUMENTS

| | | | | |
|---|---|---|---|---|
| 2007/0282629 A1* | 12/2007 | Plambeck | ........... | G06F 16/9538 |
| | | | | 600/300 |
| 2012/0155734 A1* | 6/2012 | Barratt | ................... | G06T 7/344 |
| | | | | 382/128 |

(Continued)

OTHER PUBLICATIONS

Bourigault, et al. ; Multimodal PET/CT Tumour Segmentation and Prediction of Progression-Free Survival using a Full-Scale UNet with Attention ; University of Oxford ; Nov. 6, 2021 ; 13 Pages.

(Continued)

*Primary Examiner* — Jay M. Patel
(74) *Attorney, Agent, or Firm* — Oblon, McClelland, Maier & Neustadt, L.L.P.

(57) ABSTRACT

A system, computer-readable storage medium and method for prognosis of head and neck cancer, includes an input for receiving electronic health records (EHR) of a patient, an input for receiving multimodal images of a head and neck area of the patient, a feature extraction module for converting the electronic health records and multimodal images into at least one feature vector, a hybrid machine learning architecture that includes a multi-task logistic regression (MTLR) model and a multi-layer artificial neural network, the hybrid architecture takes as input the at least one feature vector and outputs a final risk score of prognosis for head and neck cancer for the patient.

15 Claims, 19 Drawing Sheets

(56) References Cited

U.S. PATENT DOCUMENTS

| | | | |
|---|---|---|---|
| 2015/0205926 A1* | 7/2015 | McPhearson | G06Q 10/10 |
| | | | 705/2 |
| 2018/0265858 A1* | 9/2018 | Souza | B82Y 5/00 |
| 2019/0371450 A1* | 12/2019 | Lou | G06N 3/0464 |
| 2020/0063208 A1* | 2/2020 | Zhang | C12Q 1/686 |
| 2021/0017509 A1* | 1/2021 | Wu | C07K 14/705 |
| 2021/0244831 A1* | 8/2021 | Steinmetz | A61K 49/1896 |
| 2022/0181006 A1* | 6/2022 | Bremer | G06N 20/10 |
| 2022/0254439 A1* | 8/2022 | Van De Stolpe | C12Q 1/6886 |
| 2024/0175093 A1* | 5/2024 | Pitroda | G16H 50/20 |

OTHER PUBLICATIONS

Haibe-Kains, et al. ; A Machine Learning Challenge for Prognostic Modelling in Head and Neck Cancer Using Multimodal Data ; Princess Margaret Cancer Centre ; Feb. 22, 2021 ; 25 Pages.
Huang, et al. ; Fusion of medical imaging and electronic health records using deep learning: a systematic review and implementation guidelines ; Digital Medicine 136 ; 2020 ; 9 Pages.

* cited by examiner

DEEP LEARNING APPARATUS AND METHOD FOR SEGMENTATION AND SURVIVAL PREDICTION FOR HEAD AND NECK TUMORS

STATEMENT REGARDING PRIOR DISCLOSURE BY THE INVENTORS

Aspects of this technology are described in an article Saeed, N., Majzoub, R. A., Sobirov, I., & Yaqub, M. (2021 September), "An ensemble approach for patient prognosis of head and neck tumor using multimodal data," in 3D *Head and Neck Tumor Segmentation in PET/CT Challenge* (pp. 278-286), Springer, Cham. and is herein incorporated by reference in its entirety.

BACKGROUND

Technical Field

The present disclosure is directed to machine learning techniques for segmentation and cancer survival prediction (including prognosis), particularly in the case of head and neck cancer. The machine learning techniques utilize multimodal data, consisting of imaging data (CT and PET scans) and electronic health records (patient's age, gender, weight, tumor stage, chemotherapy experience, presence of human papillomavirus). The machine learning techniques include a hybrid of deep learning neural network and a multi-task logistic regression (MTLR) model.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cancers that are known collectively as head and neck cancers usually begin in the squamous cells that line the mucosal surfaces of the head and neck (for example, those inside the mouth, throat, and voice box). These cancers are referred to as squamous cell carcinomas of the head and neck. Head and neck cancers can also begin in the salivary glands, sinuses, or muscles or nerves in the head and neck, but these types of cancer are much less common than squamous cell carcinomas. Cancers of the brain, the eye, the esophagus, the thyroid gland, and the skin of the head and neck are not usually classified as head and neck cancers.

A type of head and neck cancer, known as oropharyngeal cancer is a disease in which malignant (cancer) cells form in the tissues of the oropharynx. The oropharynx is the middle part of the pharynx (throat), behind the mouth. The pharynx is a hollow tube about 5 inches long that starts behind the nose and ends where the trachea (windpipe) and esophagus (tube from the throat to the stomach) begin. Air and food pass through the pharynx on the way to the trachea or the esophagus.

The oropharynx includes a soft palate, side and back walls of the throat, tonsils, and back one-third of the tongue.

Sometimes more than one cancer can occur in the oropharynx and in other parts of the oral cavity, nose, pharynx, larynx (voice box), trachea, or esophagus at the same time. Signs and symptoms of oropharyngeal cancer include a lump in the neck and a sore throat. However, sometimes oropharyngeal cancer does not cause early signs or symptoms.

Tests that examine the mouth and throat are used to diagnose and stage oropharyngeal cancer. These tests can include physical exam, neurological exam, PET scan, and CT scan.

A physical exam and health history can involve an exam of the body to check general signs of health, including checking for signs of disease, such as swollen lymph nodes in the neck or anything else that seems unusual. The medical doctor or dentist does a complete exam of the mouth and neck and looks under the tongue and down the throat with a small, long-handled mirror to check for abnormal areas. A history of the patient's health habits and past illnesses and treatments will also be taken.

A neurological exam can involve a series of questions and tests to check the brain, spinal cord, and nerve function. The exam checks a person's mental status, coordination, and ability to walk normally, and how well the muscles, senses, and reflexes work. This may also be called a neuro exam or a neurologic exam.

A PET-CT scan is a procedure that combines the pictures from a positron emission tomography (PET) scan and a computed tomography (CT) scan. The PET and CT scans are done at the same time with the same machine. The combined scans give more detailed pictures of areas inside the body than either scan gives by itself. A PET-CT scan may be used to help diagnose disease, such as cancer, plan treatment, or find out how well treatment is working.

A CT scan (CAT scan) is a procedure that makes a series of detailed pictures of areas inside the body, such as the head, neck, chest, and lymph nodes, taken from different angles. The pictures are made by a computer linked to an x-ray machine. A dye is injected into a vein or swallowed to help the organs or tissues show up more clearly. This procedure is also called computed tomography, computerized tomography, or computerized axial tomography.

A PET scan (positron emission tomography scan) is a procedure to find malignant tumor cells in the body. A small amount of radioactive glucose (sugar) is injected into a vein. The PET scanner rotates around the body and makes a picture of where glucose is being used in the body. Malignant tumor cells show up brighter in the picture because they are more active and take up more glucose than normal cells do.

Each year, 1.3 million people are diagnosed with head and neck (H&N) cancer worldwide on average. See Wang, X., Li, B. b.: Deep learning in head and neck tumor multiomics diagnosis and analysis: Review of the literature. Frontiers in Genetics 12, 42 (2021), incorporated herein by reference in its entirety. However, the mortality rate can be lowered to 70% with early detection of H&N tumor. Therefore, diagnosis and prognosis are the two primary practices involved in most medical treatment pipelines, especially for cancer-related diseases. After determining the presence of cancer, a doctor tries to prescribe the best course of treatment yet with limited information, it is very challenging. An early survival prediction can help doctors pinpoint a specific and suitable treatment course. Different biomarkers from radiomics field can be used to predict and prognose medical cases in a non-invasive fashion. See Gillies, R. J., Kinahan, P. E., Hricak, H.: Radiomics: Images are more than pictures, they are data. Radiology 278(2), 563-577 (2016), pMID: 26579733, incorporated herein by reference in its entirety. It is used in oncology to help with cancer prognosis, allowing patients to plan their lives and actions in their upcoming days. In addition, it enables doctors to better plan for the time and mode of action followed for treatment. See Mackillop, W. J.: The Importance of Prognosis in Cancer Medicine. American Cancer Society (2006), incorporated herein by reference in its entirety. This is necessary to make more accurate predictions, which, in turn, is likely to lead to better management by the doctors.

Many other research fields also strive to assist medical doctors, at least to a point of alleviating their work process. One of the most common statistical frameworks used for the prediction of the survival function for a particular unit is the Cox proportional hazard model (CoxPH), proposed by Cox in 1972. See Cox, D. R.: Regression models and life-tables. Journal of the Royal Statistical Society: Series B (Methodological) 34(2), 187-202 (1972), incorporated herein by reference in its entirety. The CoxPH model is a regression model commonly used in medical research for investigating the association between the survival time of patients and one or more predictor variables. In other words, the CoxPH model is for examining how specified factors influence the rate of a particular event happening (e.g., infection, death) at a particular point in time. This rate is commonly referred as the hazard rate. The Cox model is expressed by the hazard function denoted by h(t), where the hazard function can be interpreted as the risk of dying at time t. Thus, the CoxPH model focuses on developing a hazard function, i.e., an age-specific failure rate. Nevertheless, CoxPH comes with specific issues, such as the fact that the proportion of hazards for any two patients is constant or that the time for the function is unspecified.

Yu et al. proposed an alternative to CoxPH-multi-task logistic regression (MTLR). See Yu, C. N., Greiner, R., Lin, H. C., Baracos, V.: Learning patient-specific cancer survival distributions as a sequence of dependent regressors. In: Shawe-Taylor, J., Zemel, R., Bartlett, P., Pereira, F., Weinberger, K. Q. (eds.) Advances in Neural Information Processing Systems. vol. 24. Curran Associates, Inc. (2011), incorporated herein by reference in its entirety. MTLR can be understood as a sequence of logistic regression models created at various timelines to evaluate the probability of the event happening. Fotso improved the original MTLR model by integrating neural networks to achieve nonlinearity, yielding higher results. See Fotso, S.: Deep neural networks for survival analysis based on a multi-task framework (2018), incorporated herein by reference in its entirety. The MTLR model takes the form of a series of logistic regression models built on different time intervals so as to estimate the probability that the event of interest happened within each interval. Fotso noted that both CoxPH and MTLR models fail to capture nonlinear elements from the data and consequently stop yielding satisfactory performance. According to Fotso, by replacing the linear core of the MTLR, the Neural Multi-Task Logistic Regression (N-MTLR) brings a lot of flexibility in the modeling, without relying on any CoxPH model assumptions.

Deep neural networks, also referred to as deep learning (DL), has gained a considerable amount of attention in classification, detection, and segmentation tasks of the medical research field. Furthermore, their use in far more complicated tasks such as prognosis and treatment has made DL even more popular, as it can handle data in large amounts and from different modalities, both tabular and visual.

Many studies have been conducted to perform prognosis of cancer using DL. Sun et al. propose a deep learning approach for the segmentation of brain tumor and prognosis of survival using multimodal MRI images. See Sun, L., Zhang, S., Chen, H., Luo, L.: Brain tumor segmentation and survival prediction using multimodal MRI scans with deep learning. Frontiers in Neuroscience 13, 810 (2019), incorporated herein by reference in its entirety. 4524 radiomic features are extracted from the segmentation outcome, and further feature extraction is performed with a decision tree and cross-validation. For survival prediction, they use a random forest model. In a similar task done by Shboul et al., a framework for glioblastoma and abnormal tissue segmentation and survival prediction is suggested. See Shboul, Z. A., Alam, M., Vidyaratne, L., Pei, L., Elbakary, M. I., Iftekharuddin, K. M.: Feature-guided deep radiomics for glioblastoma patient survival prediction. Frontiers in Neuroscience 13, 966 (2019), incorporated herein by reference in its entirety. The segmentation results, along with other medical data, are combined to predict the survival rate. Tseng et al. develop a multiclass deep learning model to analyze the historical data of oral cancer cases. See Tseng, W. T., Chiang, W. F., Liu, S. Y., Roan, J., Lin, C. N.: The application of data mining techniques to oral cancer prognosis. J. Med. Syst. 39(5), 1-7 (May 2015), incorporated herein by reference in its entirety.

Many other cancer types have been previously studied extensively, including brain, breast, liver, lung, rectal and many other cancer types. See Zhou, T., Fu, H., Zhang, Y., Zhang, C., Lu, X., Shen, J., Shao, L.: M2net: Multi-modal multi-channel network for overall survival time prediction of brain tumor patients. In: International Conference on Medical Image Computing and Computer-Assisted Intervention. pp. 221-231. Springer (2020); Sun, D., Wang, M., Li, A.: A multimodal deep neural network for human breast cancer prognosis prediction by integrating multi-dimensional data. IEEE/ACM transactions on computational biology and bioinformatics 16(3), 841-850 (2018); Gupta, N., Kaushik, B. N.: Prognosis and prediction of breast cancer using machine learning and ensemble-based training model. The Computer Journal (2021); Lee, H., Hong, H., Seong, J., Kim, J. S., Kim, J.: Survival prediction of liver cancer patients from CT images using deep learning and radiomic feature-based regression. In: Medical Imaging 2020: Computer-Aided Diagnosis. vol. 11314, p. 113143L. International Society for Optics and Photonics (2020); Chen, J., Cheung, H., Milot, L., Martel, A. L.: Aminn: Autoencoder-based multiple instance neural network improves outcome prediction in multifocal liver metastases. In: International Conference on Medical Image Computing and Computer-Assisted Intervention. pp. 752-761. Springer (2021); Zhen, S. h., Cheng, M., Tao, Y. b., Wang, Y. f., Juengpanich, S., Jiang, Z. y., Jiang, Y. k., Yan, Y. y., Lu, W., Lue, J. m., et al.: Deep learning for accurate diagnosis of liver tumor based on magnetic resonance imaging and clinical data. Frontiers in oncology 10, 680 (2020); Doppalapudi, S., Qiu, R. G., Badr, Y.: Lung cancer survival period prediction and understanding: Deep learning approaches. International Journal of Medical Informatics 148, 104371 (2021); Hosny, A., Parmar, C., Coroller, T. P., Grossmann, P., Zelcznik, R., Kumar, A., Bussink, J., Gillies, R. J., Mak, R. H., Aerts, H. J.: Deep learning for lung cancer prognostication: a retrospective multi-cohort radiomics study. PLOS medicine 15(11), e1002711 (2018); Li, H., Boimel, P., Janopaul-Naylor, J., Zhong, H., Xiao, Y., Ben-Josef, E., Fan, Y.: Deep convolutional neural networks for imaging data based survival analysis of rectal cancer. In: 2019 IEEE 16th International Symposium on Biomedical Imaging (ISBI 2019). pp. 846-849. IEEE (2019), each incorporated by reference in their entirety. Long-term survival prediction using 33 different types of cancer was examined in-depth in Vale-Silva et al. See Vale-Silva, L. A., Rohr, K.: Long-term cancer survival prediction using multimodal deep learning. Scientific Reports 11(1), 1-12 (2021), incorporated by reference in its entirety. Their MultiSurv multimodal network is compromised of several submodules responsible for feature extraction, representation fusion, and prediction. As in Sun et al., multimodal deep neural network using gene expression profile, copy-number alteration profile, and clinical data was proposed in for breast cancer prognosis. In Chen et al., an improvement on the prognosis of patients with colorectal cancer liver metastases was studied. The authors proposed an end-to-end autoencoder neural network for this task utilizing radiomics features taken from MRI images. For overall survival prediction of patients with brain cancer, authors in Zhou et al. proposed an end-to-end model that extracts features from MRI images, fuses them, and combines outputs of modality-specific submodels to produce the survival prediction. See Zhou, T., Fu, H., Zhang, Y., Zhang, C., Lu, X., Shen, J., Shao, L.: M2net: Multi-modal multi-channel network for overall survival time prediction of brain tumor patients. In: International Conference on Medical Image Computing and Computer-Assisted Intervention. pp. 221-231. Springer (2020).

A few studies have been conducted for the prognosis of H&N cancer. See Kazmierski, M., Welch, M., Kim, S., McIntosh, C., Head, P. M., Group, N. C., Rey-McIntyre, K., Huang, S. H., Patel, T., Tadic, T., Milosevic, M., Liu, F. F., Hope, A., Bratman, S., Haibe-Kains, B.: A machine learning challenge for prognostic modelling in head and neck cancer using multi-modal data (2021), incorporated herein by reference in its entirety. The prognosis studied in Parmar et al. shows that they achieve the area under the curve (AUC) of 0.69 for their best-performing dataset for H&N tumor, while for the rest of the datasets, they achieve AUC between 0.61 and 0.68. See Parmar, C., Grossmann, P., Rietveld, D., Rietbergen, M. M., Lambin, P., Aerts, H. J. W. L.: Radiomic machine-learning classifiers for prognostic biomarkers of head and neck cancer. Frontiers in Oncology 5, 272 (2015), incorporated herein by reference in its entirety. Furthermore, Kazmierski et al use electronic health record (EHR) data and pre-treatment radiological images to develop a model for survival prediction in H&N cancer. Out of the many trials they experimented with, a non-linear, multitask approach that uses the EHR data and tumor volume produced the highest result for prognosis. Clinically, H&N squamous cell carcinoma refers to different types of H&N cancers, including oropharynx cancer. See Johnson, D. E., Burtness, B., Leemans, C. R., Lui, V. W. Y., Bauman, J. E., *Grandis*, J. R.: Head and neck squamous cell carcinoma. Nature reviews Disease primers 6(1), 1-22 (2020), incorporated herein by reference in its entirety. Authors in Diamant et al. studied H&N squamous cell carcinoma, creating an end-to-end network and arguing that a basic CNN-based model can extract more informative radiomics features from CT scans to predict H&N cancer treatment outcomes. See Diamant, A., Chatterjee, A., Valli eres, M., Shenouda, G., Seuntjens, J.: Deep learning in head & neck cancer outcome prediction. Scientific reports 9(1), 1-10 (2019), incorporated herein by reference in its entirety. H&N squamous cell carcinoma prognosis and its recurrence using DL were examined in FH et al. See FH, T., CYW, C., EYW, C.: Radiomics ai prediction for head and neck squamous cell carcinoma (hnscc) prognosis and recurrence with target volume approach. BJR—Open 3, 20200073 (2021), incorporated herein by reference in its entirety. The authors used CT scans of patients diagnosed with this type of cancer and extracted radiomics features manually using gross tumor volume and planning target volume. They predicted H&N cancer-related death and recurrence of cancer using a DL-driven model. Oropharyngeal squamous cell carcinoma, in particular, was a topic of interest in Fujima et al. See Fujima, N., Andreu-Arasa, V. C., Meibom, S. K., Mercier, G. A., Truong, M. T., Hi-rata, K., Yasuda, K., Kano, S., Homma, A., Kudo, K., et al.: Prediction of the local treatment outcome in patients with oropharyngeal squamous cell carcinoma using deep learning analysis of pretreatment FGD-PET images. BMC cancer 21(1), 1-13 (2021), incorporated herein by reference in its entirety. PET scans were used to train different popular CNN architectures, such as AlexNet, GoogleLeNet, and ResNet, all of which were pretrained on ImageNet, to compare it with the traditional methods that are trained on clinical records. By comparing all four different approaches, they concluded that using PET scans for a diagnostic DL model can predict progression-free survival and treatment outcome. See Krizhevsky, A., Sutskever, I., Hinton, G. E.: Imagenet classification with deep convolutional neural networks. Advances in neural information processing systems 25, 1097-1105 (2012); Szegedy, C., Liu, W., Jia, Y., Sermanet, P., Reed, S., Anguelov, D., Erhan, D., Vanhoucke, V., Rabinovich, A.: Going deeper with convolutions. In: Proceedings of the IEEE conference on computer vision and pattern recognition. pp. 1-9 (2015); He, K., Zhang, X., Ren, S., Sun, J.: Deep residual learning for image recognition. In: Proceedings of the IEEE conference on computer vision and pattern recognition. pp. 770-778 (2016); Deng, J., Dong, W., Socher, R., Li, L. J., Li, K., Fei-Fei, L.: Imagenet: A large-scale hierarchical image database. In: 2009 IEEE conference on computer vision and pattern recognition. pp. 248-255. IEEE (2009).

Still, such results for the task of prognosis of H&N cancer are unlikely to motivate clinicians to use machine learning models in clinical practice; therefore, more accurate prognosis is critical to help solve this problem.

It is one object of the present disclosure to provide a solution including a multimodal machine learning algorithm, method and system that, without prior information on the exact location of the tumor, utilizes both tabular and imaging data for the prognosis of Progression Free Survival (PFS) for patients who have H&N oropharyngeal cancer. It is an object of the present disclosure to address the prognosis task of the MICCAI 2021 HEad and neCK TumOR segmentation and outcome prediction in PET/CT images challenge (HECKTOR). See Overview of the HECKTOR challenge at MICCAI 2021: Automatic Head and Neck Tumor Segmentation and Outcome Prediction in PET/CT images. Vincent Andrearczyk, Valentin Oreiller, Sarah Boughdad, Catherine Chez Le Rest, Hesham Elhalawani, Mario Jreige, John O. Prior, Martin Vallieres, Dimitris Visvikis, Mathieu Hatt, Adrien Depeursinge, LNCS challenges, 2021; and Head and Neck Tumor Segmentation in PET/CT: The HECKTOR Challenge, Valentin Oreiller et al., Medical Image Analysis, 2021 (under revision), each incorporated herein by reference in their entirety.

SUMMARY

An aspect is a system for prognosis of head and neck cancer, that can include processing circuitry having an input for receiving electronic health records (EHR) of a patient; an input for receiving multimodal images of a head and neck area of the patient; a feature extraction module for converting the electronic health records and multimodal images into at least one feature vector; and a hybrid machine learning architecture that includes a multi-task logistic regression (MTLR) model and a multi-layer artificial neural network, the hybrid architecture takes as input the at least one feature vector and displays a final risk score of prognosis for head and neck cancer for the patient.

A further aspect is a method for prognosis of head and neck cancer, the method can include receiving, via electronic circuitry, electronic health records (EHR) of a patient; receiving, via the electronic circuitry, multimodal images of the head and neck area of the patient; converting, via the electronic circuitry, the electronic health records and multimodal images into at least one feature vector; receiving, by a hybrid architecture, the at least one feature vector, wherein the hybrid machine learning architecture includes a multi-task logistic regression (MTLR) model and a multi-layer artificial neural network; and displaying a final risk score of prognosis for head and neck cancer for the patient.

A further aspect is a non-transitory computer-readable storage medium storing instructions, which when executed by processing circuitry perform a method for prognosis of head and neck cancer, that can include receiving, via electronic circuitry, electronic health records (EHR); receiving, via the electronic circuitry, multimodal images of the head and neck area of a patient; converting, via the electronic circuitry, the electronic health records and multimodal images into at least one feature vector; and a hybrid machine learning architecture that includes a multi-task logistic regression (MTLR) model and a multi-layer artificial neural network, the method comprising receiving, by the hybrid architecture, the at least one feature vector and displaying a final risk score of prognosis for head and neck cancer.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 4A illustrates the CT slice, FIG. 4B illustrates the PET slice, FIG. 4C illustrates the mask superimposed on the CT image;

FIG. 5A illustrates male-to-female ratio, FIG. 5B illustrates distribution of age, FIG. 5C illustrates the TNM edition for all patients;

FIG. 6A illustrates the survival rate for males and females, FIG. 6B illustrates the metastasis effects on the survival of patients;

FIG. 7A illustrates the CT scan with a rectangle of a region to be cropped, FIG. 7B illustrates the PET scan and the cropping region, FIG. 7C illustrates the fused image in the cropped form;

FIG. 11A illustrates the original PET scan, FIG. 11B illustrates the original CT scan and an imposed ground truth mask, FIG. 11C illustrates a cropped PET, FIG. 11D illustrates a cropped CT with a ground truth mask;

DETAILED DESCRIPTION

Figure 1:
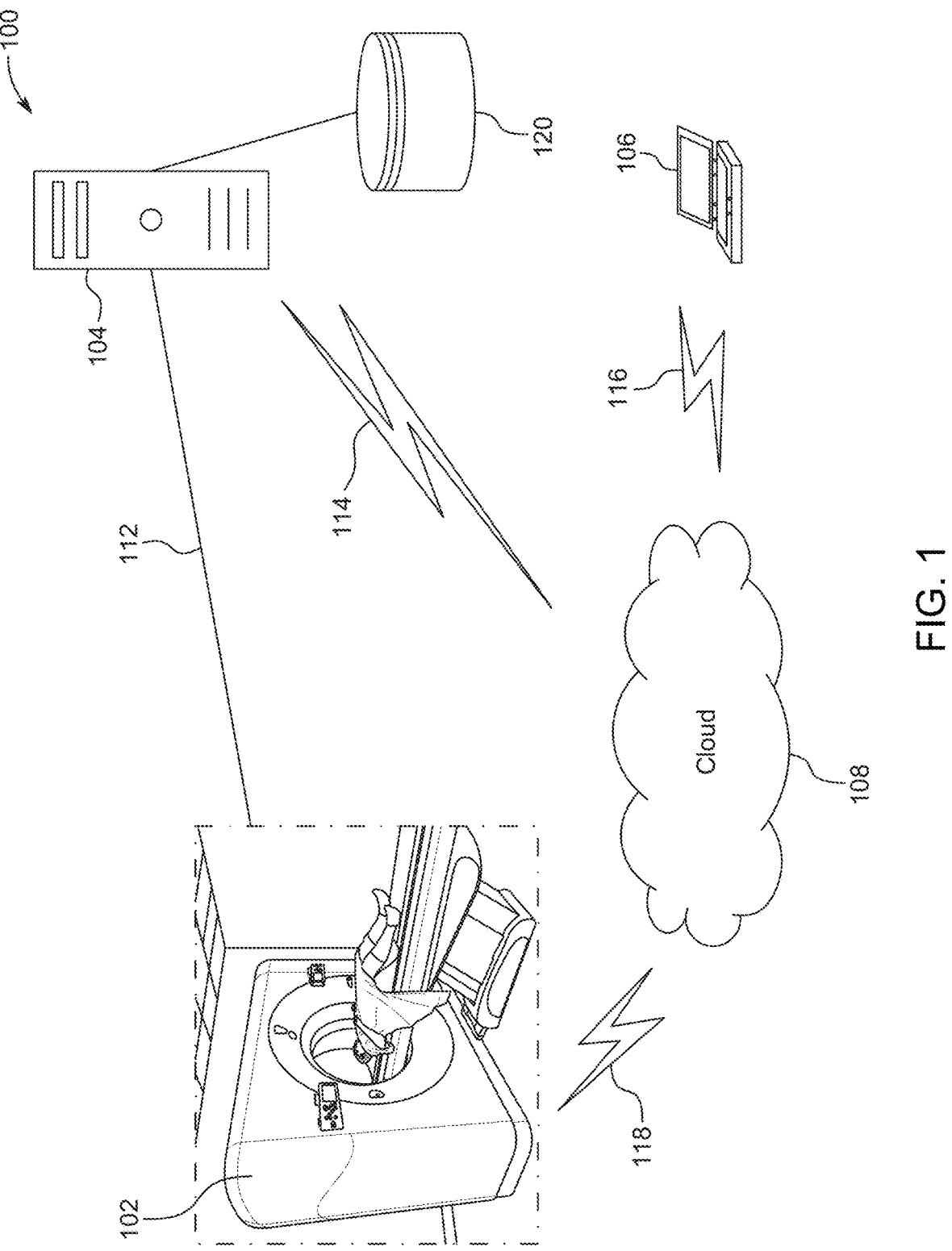
FIG. 1 is a system diagram of a clinic for cancer treatment.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Doctors and medical researchers strive for more efficient treatments and better care for cancer patients. One type of cancer, Head and Neck (H&N) cancer is a collective term used to describe malignant tumors that develop in the mouth, nose, throat, or other head and neck areas. Accurate prognosis is important to patients as well. When diagnosed with cancer, most patients ask about their prognosis: "how long will I live", and "what is the success rate of each treatment option". Many doctors provide patients with statistics on cancer survival based only on the site and stage of the tumor. Commonly used statistics include the 5-year survival rate and median survival time, e.g., a doctor can tell a specific patient with early stage cancer that s/he has a 50% 5-year survival rate. Although such estimates do apply to the population in general, they are not particularly accurate for individual patients, as they do not take into account patient-specific information such as age and general health conditions.

On the other hand, doctors routinely conduct different types of scans like computed tomography (CT) and positron emission tomography (PET) in clinics and utilize them to extract biomarkers of the tumor area that is used with other information like the patient electronic health records (EHR) for treatment plans. Automatic prognosis and segmentation can significantly influence the treatment plan by speeding up the process and achieving robust outcomes.

Both gross tumor volume (GTV) delineations in radiotherapy planning and radiomics analyses aiming at predicting outcome rely on an expensive and error-prone manual or semi-automatic annotation process of Volumes of Interest (VOI) in three dimensions. The fully automatic segmentation of H&N tumors from FDG-PET/CT images could therefore enable faster and more reproducible GTV definition as well as the validation of radiomics models on very large cohorts. By focusing on metabolic and morphological tissue properties respectively, PET and CT images provide complementary and synergistic information for cancerous lesion segmentation and patient outcome prediction. The HEad and neCK TumOR segmentation and outcome prediction from PET/CT images (HECKTOR) challenge aimed at identifying the best methods to leverage the rich bi-modal information in the context of H&N primary tumor segmentation and outcome prediction.

The HECKTOR challenge is composed of three tasks related to the automatic analysis of PET/CT images for patients with Head and Neck cancer (H&N), focusing on the oropharynx region. Task 1 is the automatic segmentation of H&N primary Gross Tumor Volume (GTVt) in FDG-PET/CT images. Task 2 is the automatic prediction of Progression Free Survival (PFS) from the same FDG-PET/CT. Finally, Task 3 is the same as Task 2 with ground truth GTVt annotations provided to the participants. The data were collected from six centers for a total of 325 images, split into 224 training and 101 testing cases. The challenge was highlighted by participation of 103 registered teams and 448 result submissions. The best methods obtained a Dice Similarity Coefficient (DSC) of 0.7591 in the first task, and a Concordance index (C-index) of 0.7196 and 0.6978 in Tasks 2 and 3, respectively.

The C-index is a widely used metric for the global evaluation of prognostic models in survival analysis. A good model according to the C-index (C=1) is one that always assigns higher scores to the subjects who experience the earlier events. An embodiment of the disclosed invention achieved the top rank for Task 2 of the HECKTOR challenge, with a C-index of 0.72.

FIG. 1 is a system in a clinic for cancer treatment. In a typical clinic 100, an oncologist will have access to imaging devices 102 for obtaining scans of computed tomography (CT) and positron emission tomography (PET), or at least access to the CT/PET scanned images stored in a database 120, as well as access to patient electronic health records, for example, via a computer terminal, laptop computer, tablet computer, or other electronic device 106 capable of accessing an electronic medical record (EMR) computer database. The EMR database may be stored locally 120 for patients of the clinic or may be stored in a remote centralized system, such as in a cloud service 108, or a combination of local storage and remote storage. The clinic 100 may have, or be connected to, one or more server computers 104, or workstations. Various devices in the clinic 100 may communicate via the Internet or other networking protocol, such as Bluetooth. Communications may be performed either via a wired connection 112 and/or wireless connection 114, 116, 118. Internet communications may include access to a cloud service 108. Database storage may be maintained in the cloud service 108.

Figure 2:
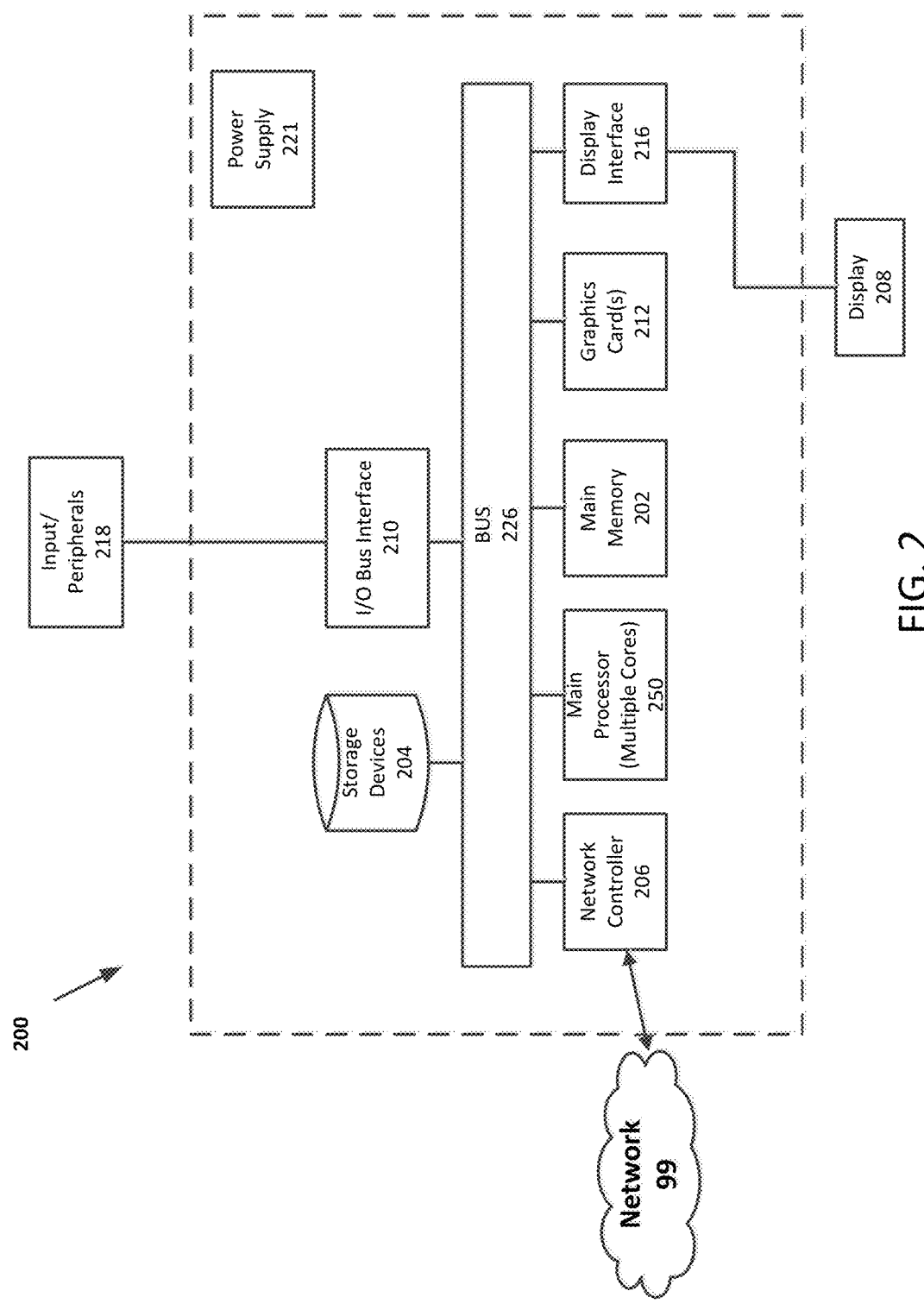
FIG. 2 is a block diagram of a computer workstation capable of implementing machine learning algorithms.

FIG. 2 is a block diagram illustrating an example computer system for implementing the multimodal machine learning algorithm according to an exemplary aspect of the disclosure. The computer system may be a server or workstation running a server operating system, for example Windows Server, a version of Unix OS, or Mac OS Server. The computer system 200 may include processing circuitry, including one or more processing cores 250 and graphics processing units (GPU), provided on at least one graphics card 212. The graphics processing units may perform many of the mathematical operations of the machine learning algorithm. The computer system 200 includes main memory 202, typically random access memory RAM, which contains the software being executed by the processing cores 250 and graphics processing units, as well as a non-volatile storage device 204 for storing data and the software programs.

Several interfaces for interacting with the computer system 200 may be provided, including an I/O Bus Interface 210, Input/Peripherals 218 such as a keyboard, touch pad, mouse, Display Interface 216 and one or more Displays 208, and a Network Controller 206 to enable wired or wireless communication through a network 99. The interfaces, memory and processors may communicate over the system bus 226. The computer system 200 includes a power supply 221, which may be a redundant power supply.

In an exemplary implementation, machine learning models may be trained in a computer workstation 200 having a graphics card 212 optimized for training deep learning models. In an example implementation, the computer workstation 200 includes a single GPU NVIDIA RTX A6000 graphics card with 48 GB of synchronous graphics random-access memory. The RTX A6000 has multiple GPU processing cores including 10,752 CUDA cores, 336 Tensor Cores, and 84 RT cores. The GPU processing cores are programmed with a machine learning package that is configured to run program code on the GPU, such as CUDA and cuDNN. In an exemplary embodiment, the PyTorch machine learning framework was used to develop the disclosed machine learning models. A known alternative framework is the TensorFlow framework. PyTorch is a library for Python programs that facilitates building deep learning projects. PyTorch emphasizes flexibility and allows deep learning models to be expressed in idiomatic Python. The PyTorch library supports GPU implementation.

In an embodiment, the program code for the machine learning models is stored in a repository maintained in a storage medium, The storage medium may be an non-transitory computer readable storage medium, including, but not limited to a local storage medium such as a hard disk, a removable storage medium such as a USB flash drive, or in a cloud service.

The embodiment that achieved the top rank for Task 2 is a multimodal machine learning approach that, without prior information on the exact location of the tumor, utilizes both tabular and imaging data for the prognosis of Progression Free Survival (PFS) for patients who have H&N oropharyngeal cancer.

Figure 3:
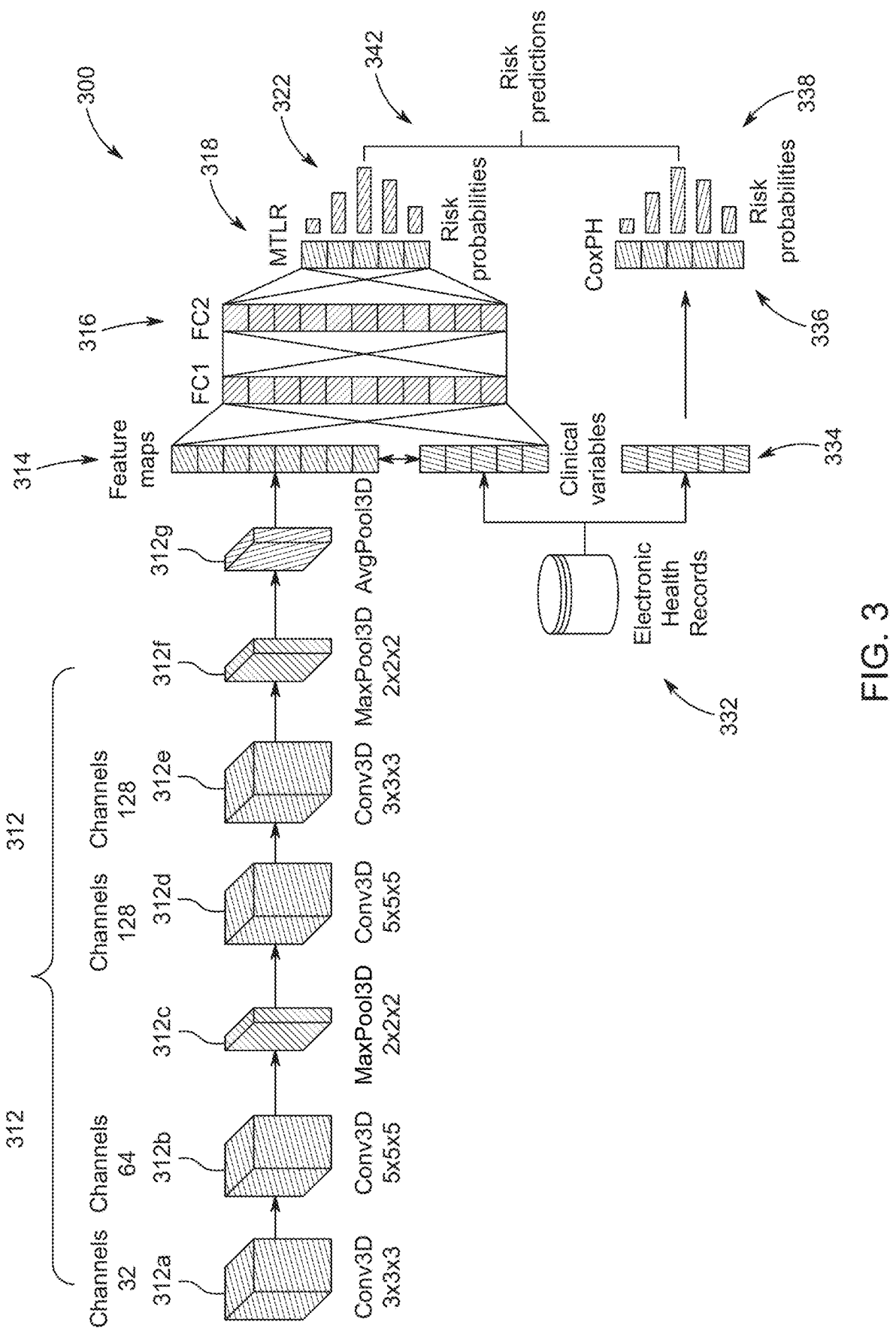
FIG. 3 is a block diagram of an overall architecture of a multimodal machine learning algorithm in accordance with an exemplary aspect of the disclosure.

FIG. 3 is a block diagram of an overall architecture for the multimodal machine learning approach that was used in Task 2 of the HECKTOR challenge in accordance with an exemplary aspect of the disclosure. The neural network architecture 300 shown in FIG. 3 is used to output risk score predictions for an individual patient. A trained neural network 300 takes as input CT and PET scans, fused or independent, and an EHR for a single patient and produces a predicted risk score anti-concordant with the Progression Free Survival in days regarding the prognosis of H&N cancer. Although a trained neural network 300 may provide a Progression Free Survival (PFS) in days, the PFS may be in other periods including months, years, or even hours.

The neural network architecture 300, as implemented using PyTorch, includes an optimized Deep-CR network with two blocks 312. Each block 312 consists of two 3D convolutional layers, each followed by ReLU activation and batch normalization 312a, 312b, 312d, 312c. The 3D CNN blocks are followed by respective 3D MaxPooling layers 312c, 312f, as well as an average pooling layer 312g. The kernel sizes of the 3D CNN layers in each block are 3 (312a, 312d) and 5 (312b, 312e), respectively. The number of output channels of the 3D CNN layers are 32, 64, 128 and 256, respectively. The number of neurons in the two feed forward layers FC1, FC2 316 are 256 each. The batch size, learning rate, and dropout were experimentally set to 16, 0.016, and 0.2, respectively, for the training. In an example implementation, the model was trained for 100 epochs using Adam optimizer on a single GPU NVIDIA RTX A6000 (48 GB) graphics card 212.

In some embodiments, the neural network architecture 300 was implemented as two variants; (variant V1) with three 3D convolution neural network (CNN) paths that take three types of image inputs (CT, PET, and fused images) and (variant V2), which includes one 3D CNN path with a single image input (the fused data) as shown in FIG. 3. Each 3D CNN outputs a feature vector 314 of length 256. In Deep Fusion V1, the 3 feature vectors are concatenated. The concatenated feature vector was then combined with EHR data 332 (clinical variables vector 334) to train two fully connected (FC) layer 316 followed by one MTLR layer 318 to estimate the risk score. Finally, the risk predictions 322 from the MTLR layers 318 and CoxPH (CoxPH layer 336) results 338 are averaged to calculate the final risk scores 342.

The CoxPH model computes a hazard function h(t).

$$h(t)=h_0(t)\exp(b_1x_1+b_2x_2+ \ldots +b_px_p)$$

where, t represents the survival time $h(t)$ is the hazard function determined by a set of p covariates $(x_1, x_2, \ldots, x_p)$ the coefficients $(b_1, b_2, \ldots, b_p)$ measure the impact (i.e., the effect size) of covariates the term $h_0$ is called the baseline hazard. It corresponds to the value of the hazard if all the xi are equal to zero (the quantity exp(0) equals 1).

In Deep Fusion V2 (FIG. 3), features are extracted from fused CT and PET scans using a CNN network 312 and concatenated with the EHR features 332. The output concatenation 314 is passed to fully connected (FC) layers 316, then to the MTLR model 318. Risk scores 322, 338 from MTLR 318 and CoxPH 336 models are averaged to get the final risk predictions 342.

Figure 4A:
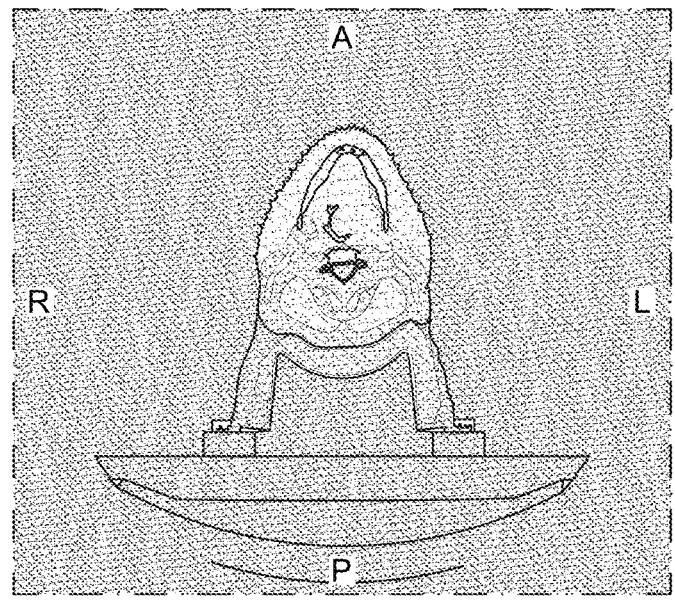
FIGS. 4A, 4B, 4C are examples from the training set of HECKTOR 2021.
Figure 4B:
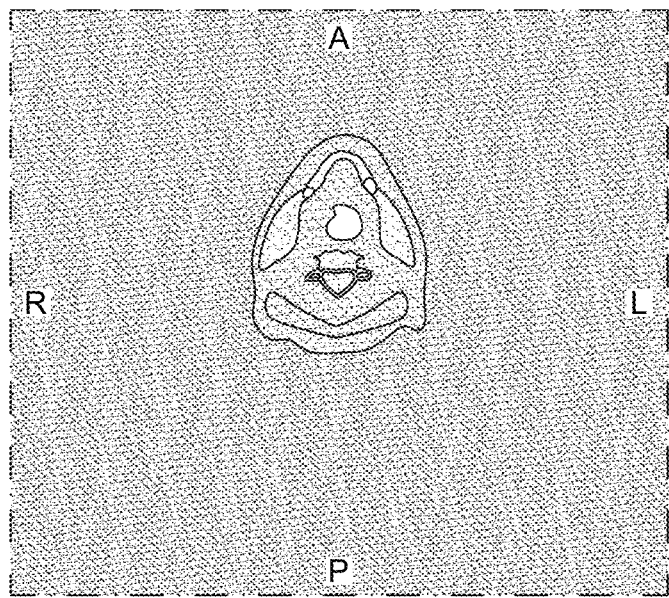
Figure 4C:
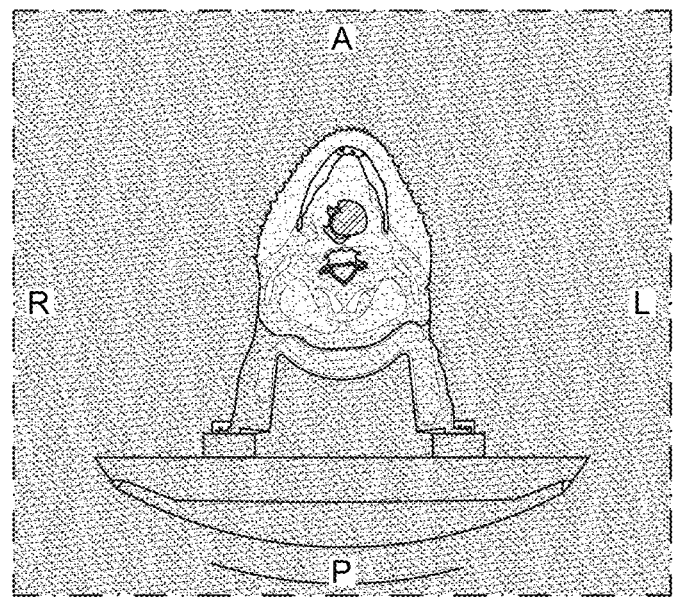

The dataset used to train the neural network models was the datasets provided by the HECKTOR committee. FIGS. 4A, 4B, 4C are examples from the training data set of HECKTOR 2021, FIG. 4A illustrates the CT slice, FIG. 4B illustrates the PET slice, FIG. 4C illustrates the mask superimposed on the CT image.

The HECKTOR committee provided CT and PET scans, manual segmentation masks and electronic health record (EHR) dataset. See, Andrearczyk et al.; Oreiller et al. The ground truth segmentation masks for H&N oropharyngeal cancer was manually delineated by oncologists as shown in FIGS. 4A, 4B, 4C. EHR contains data about a patient's age, gender, weight, tumor stage, tobacco and alcohol consumption, chemotherapy experience, presence of human papillomavirus (HPV) and other data. A clinically relevant endpoint was provided in the training set to predict PFS for each patient. The data is multi-centric, collected from four centers in Canada, one center in Switzerland and another one in France. The total number of patients involved in the study was 325, out of which 224 were training cases and 101 test cases. However, some data points are missing in the EHR, e.g., tobacco and alcohol data were only provided by one of the centers mentioned above in the training set. The dataset has 75% of the patients censored, who might have stopped following up or changed the clinic.

Figure 5A:
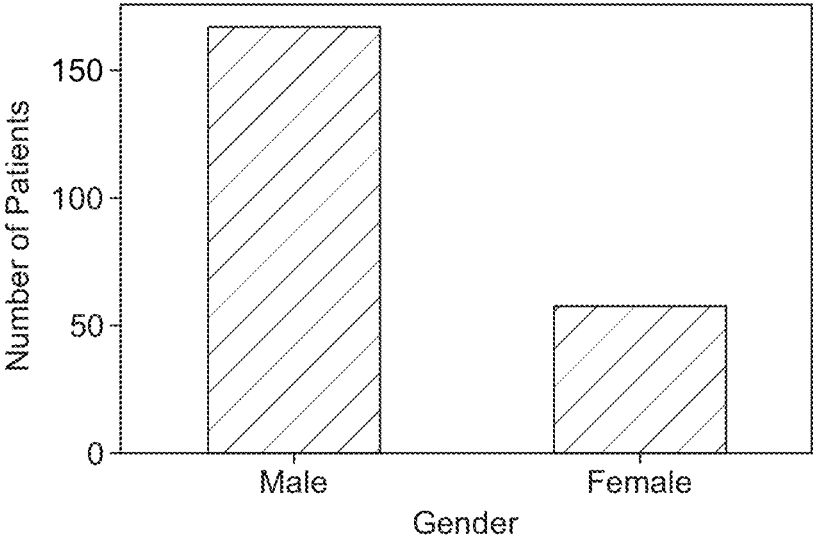
FIGS. 5A, 5B, 5C are graphs of EHR data.
Figure 5B:
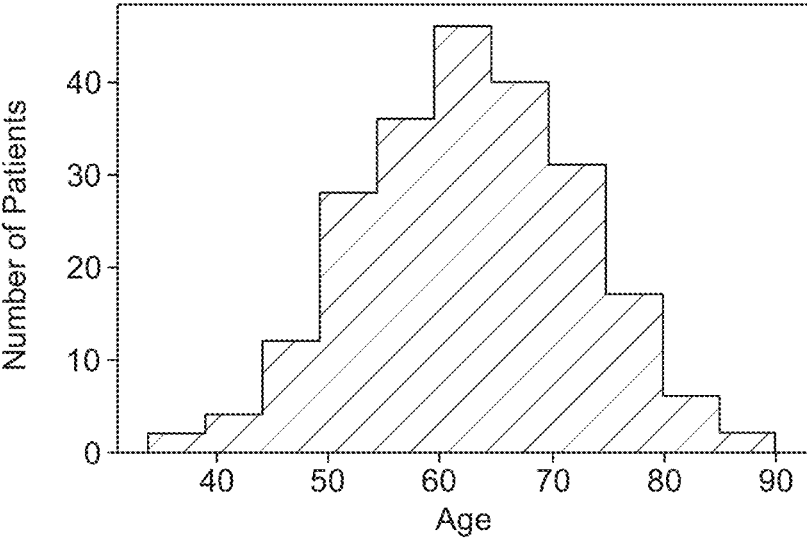
Figure 5C:
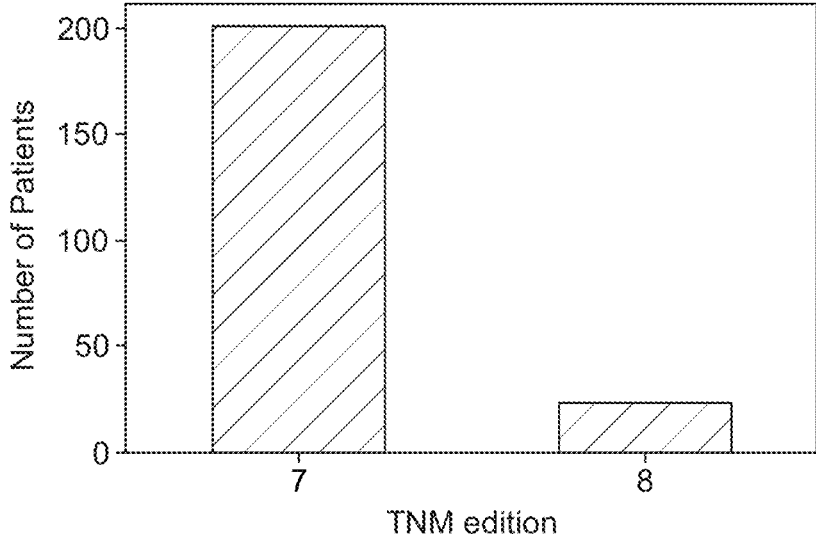

FIGS. 5A, 5B, 5C are graphs of EHR data, FIG. 5A illustrates male-to-female ratio, FIG. 5B illustrates distribution of age, FIG. 5C illustrates the TNM edition for all patients.

Visualization of the EHR data was performed to observe the distribution of patients in terms of gender and age, as shown in FIGS. 5A, 5B, 5C. Most of the patients are males, and the age ranges between 35 to 90 years with the peak at around 60 years. The TNM (T: tumor, N: nodes, and M: metastases) edition 7 is used for most patients to describe the volume and spread of cancer in a patient's body, while the rest of the patients' cases were represented using TNM edition 8.

Image preprocessing and data analysis was performed on the training dataset provided by the HECKTOR committee.

Figure 6A:
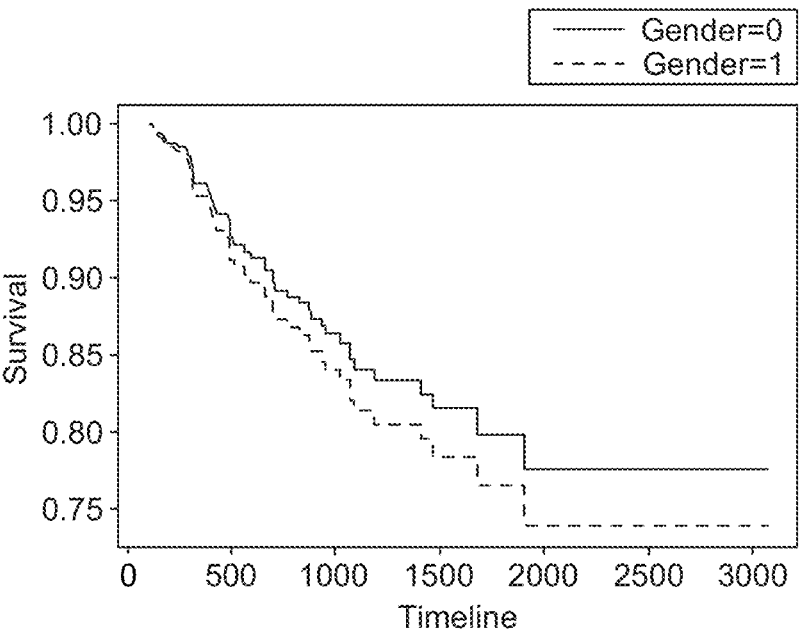
FIGS. 6A, 6B are graphs for effects on outcome when covariates are varied.
Figure 6B:
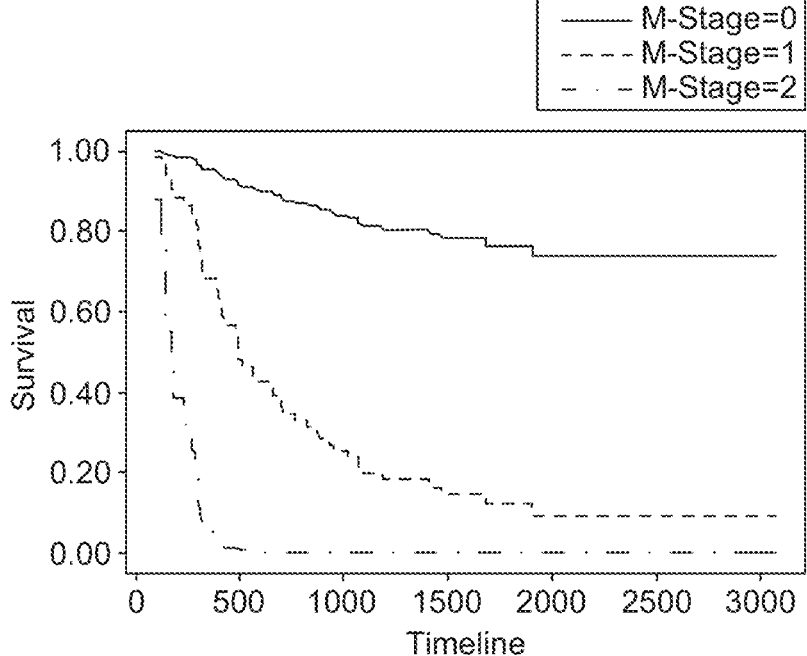

Initially, the EHR data from the training dataset are analyzed using the CoxPH model by splitting them into training, validation and testing sets to experiment on different hyperparameters and configurations of the solution. Then, the effects of different covariates on the survival rate were observed using the trained CoxPH model. FIGS. 6A, 6B are graphs for effects on outcome when covariates are varied, FIG. 6A illustrates the survival rate for males and females, FIG. 6B illustrates the metastasis effects on the survival of patients. In FIG. 6A, the gender covariate is varied by assigning males and females the values 0 and 1 respectively. The results show that the survival rate of males is less than that of females. Similarly, to observe the effect of metastasis (M), M1, M2, and Mx are assigned the values 0, 1, and 2 respectively. The analysis shows that the patients with cancer spread to other parts of their bodies (M1) have lower survival rates, which is in line with the medical science. Some data points for tobacco and alcohol were not available, so missing values were assigned values of 1 for consumers, −1 for non-consumers and 0 for patients with missing tobacco and alcohol consumption data. Then, another approach was used where the use of incomplete data features were dropped and instead trained the model on other available data features. The obtained results of the cross validation revealed that dropping incomplete data points leads to better prognosis results than imputing other available values for them.

Figure 7A:
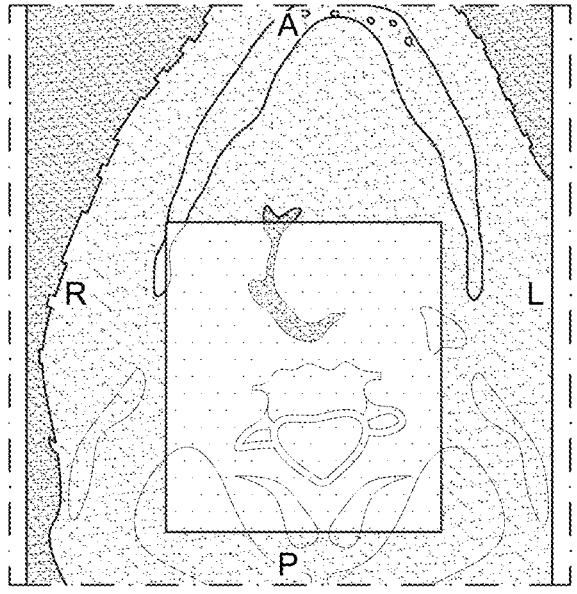
FIGS. 7A, 7B, 7C are example images for combining CT and PET scans.
Figure 7B:
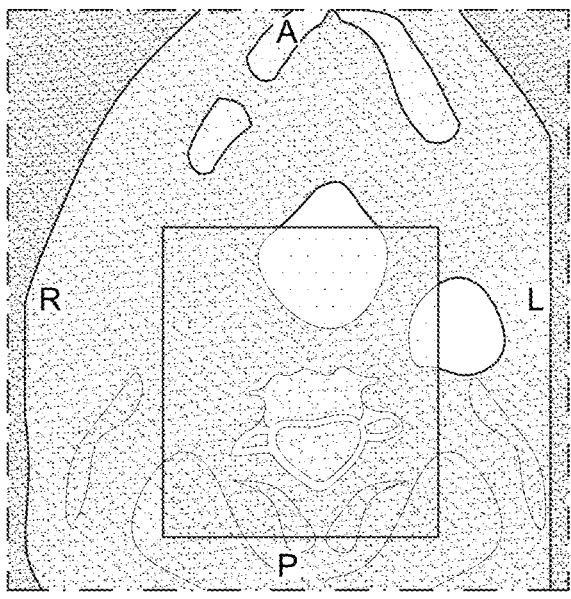
Figure 7C:
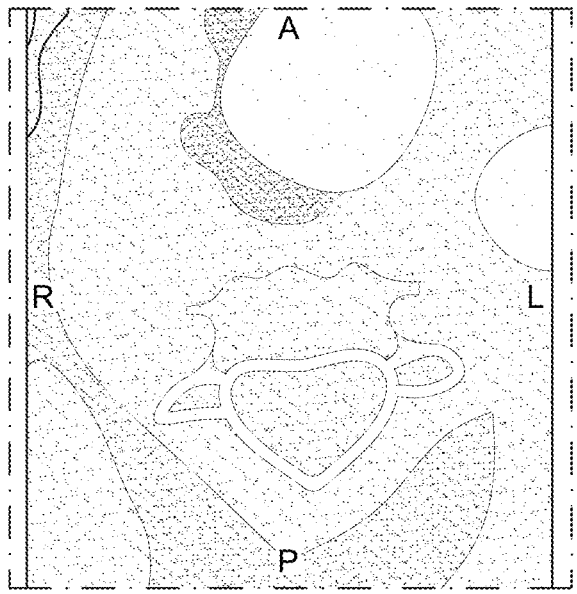

FIGS. 7A, 7B, 7C are example images for combining CT and PET scans, FIG. 7A illustrates the CT scan with a rectangle of a region to be cropped, FIG. 7B illustrates the PET scan and the cropping region, FIG. 7C illustrates the fused image in the cropped form.

As for the image dataset, PET and CT scans were preprocessed using the bounding box information available in the provided csv file to obtain 144×144×144 cropped images. To prepare the image data for the model input, the two images were normalized to the same scale and a fused image was created by averaging the two scans for each patient. To further reduce the volume, the fused output image is cropped again based on a specific distance away from the center of the 144×144×144 cube as shown in FIGS. 7A, 7B, 7C. Two possible crop resolutions were considered: 50×50×50 and 80×80×50; however, the latter was adopted since it resulted in a better outcome.

Next, the development of the machine learning model including that shown in FIG. 3 will be described. In developing the architecture of FIG. 3, a baseline arrangement began with an MTLR model as its cornerstone and was later expanded and developed by integrating and optimizing features obtained from different inputs. First, from the EHR data provided in the training dataset, a prognostic model was developed. Then, the baseline MTLR was optimized by experimenting with different hyperparameters such as learning rates, the depth and width of the feedforward layers, and the constant C in $l_2$ regularization term of the loss function of MTLR from Jin depicted in the following equation:

$$\min_{\theta} \frac{C}{2}\sum_{j=1}^{m}\|\vec{\theta}_j\|^2 = \sum_{i=1}^{n}\left[\sum_{j=1}^{m}y_j(s_i)\left(\vec{\theta}_j\cdot\vec{x}_i + b_j\right) - \log\sum_{k=0}^{m}\exp f_\theta(\vec{x}_i, k)\right]$$

The smoothness of the predicted survival curves depends on the change between consecutive timepoints and is controlled by C. See Jin, P.: Using survival prediction techniques to learn consumer-specific reservation price distributions (2015), incorporated herein by reference in its entirety.

Next, the effect of multimodality on the performance of the model was investigated by integrating the available image data. Features were extracted from the fused crops through the use of a 3D convolutional neural network (CNN) adopted from Kim et al. named Deep-CR. See Kim, S., Kazmierski, M., Haibe-Kains, B.: Deep-cr mtlr: a multimodal approach for cancer survival prediction with competing risks (2021), incorporated herein by reference in its entirety. Unlike Kim et al., the 3D CNN architecture 312 was optimized using OPTUNA framework to obtain the best hyperparameters, including the kernel sizes and the number of layers. See Akiba, T., Sano, S., Yanase, T., Ohta, T., Koyama, M.: Optuna: A next-generation hyperparameter optimization framework. CoRR abs/1907.10902 (2019), incorporated herein by reference in its entirety. These features were concatenated with tabular data and fed into two fully connected layers FC1, FC2 316. Finally, the risk 322 was calculated using the MTLR 318, and the output 322 was averaged with CoxPH model risk output 338 to obtain final risk predictions 342.

The MTLR 318 includes a non-linear transformation in place of the linear core of the original MTLR.

$\psi$ is the nonlinear transformation using $\vec{x}$ feature vector as its input. Its output is a J vector whose values are mapped to the J subdivisions of the time axis, and $$Z(\psi(\vec{x})) = \sum_{j=1}^{J}\exp\left(\sum_{l=j+1}^{J}\psi(\vec{x})\right)$$

Figure 8:
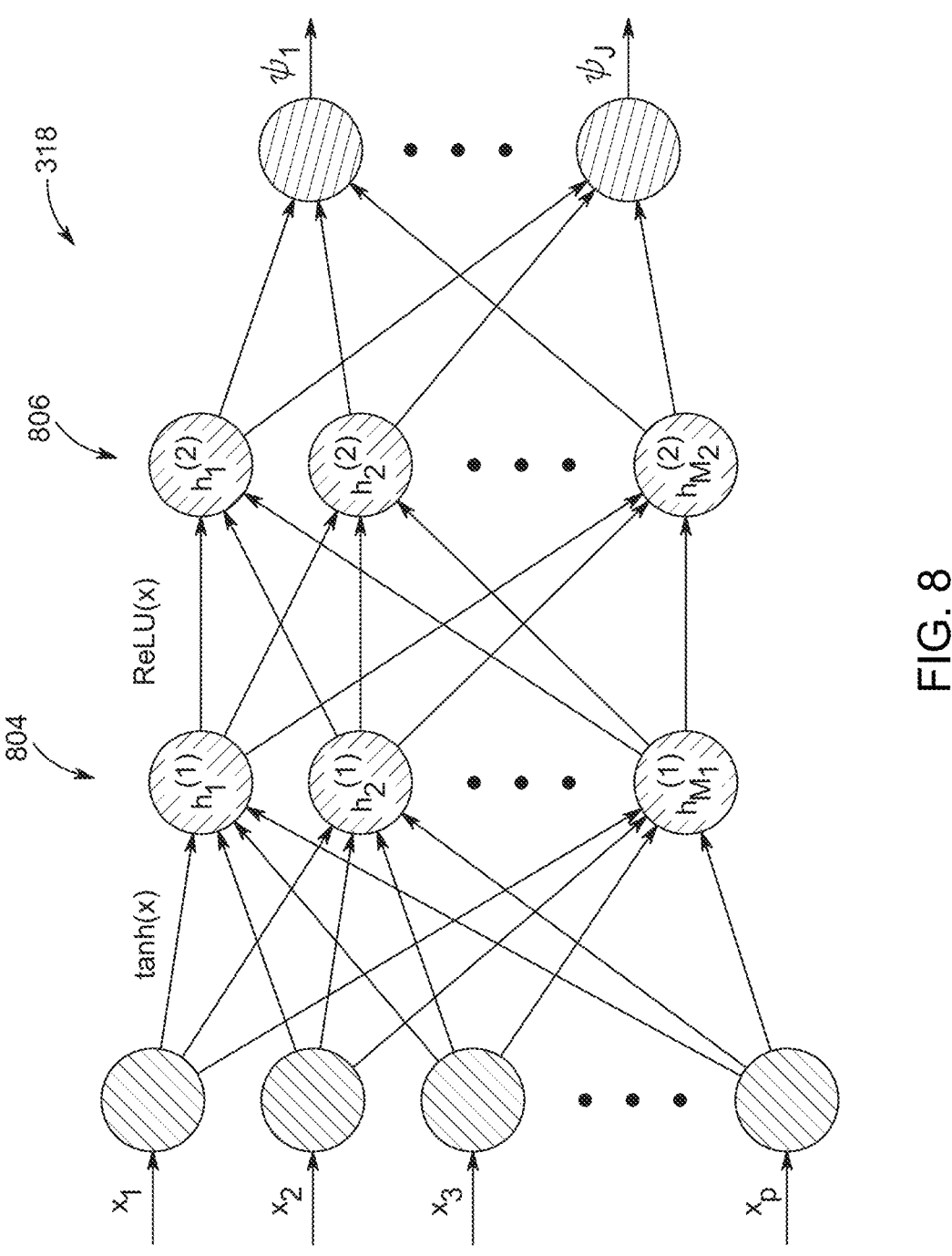
FIG. 8 is an example feed forward neural network with two hidden layers for implementing the nonlinear transformation function of the MTLR.

FIG. 8 is an example feed forward neural network with two hidden layers for implementing the nonlinear transformation function of the MTLR. Layer 804 has M1 units and h(1)(x)=tanh (x) as its activation function; Layer 806 has M2 units and h(2)(x)=ReLU(x) as its activation function.

Each of the models were trained using all the training data before applying it on the HECKTOR test set. The concordance index (C-index), one of several metrics used to measure the performance of a prognosis model, was used to report the results on the HECKTOR test dataset on each of the different models as shown in Table 1. See Allende, A. S.: Concordance index as an evaluation metric. medium.com/analytics-vidhya/concordance-index-72298c11eac7 (October 2019), incorporated herein by reference in its entirety. The baseline model which only uses MTLR to estimate the risk has 0.66 C-index. Slight improvement on C-index was achieved when combining image features and EHR in the MTLR+Deep-CR model (C-index of 0.67). The results obtained using Deep Fusion (V1) has also achieved a C-index score of 0.67. However, the best estimation of risk was obtained using Deep Fusion (V2) in FIG. 3 with C-index of 0.72.

TABLE 1

| C-index scores obtained on the HECKTOR 2021 testing dataset. | |
|---|---|
| Model | C-index |
| MTLR (Baseline) | 0.66 |
| MTLR + Deep-CR | 0.67 |
| MTLR + CoxPH + Deep Fusion (V1) | 0.67 |
| MTLR + CoxPH + DeepFusion (V2) | 0.72 |

The results of the Deep Fusion (V1) suffered a low score of 0.67 C-index compared to the (V2). This augmentation-like approach of feeding CT, PET and Fused version into individual CNN architectures, combining the outputs and forwarding them into MTLR, then finally concatenating them with CoxPH results was hypothesized to yield better results. However, C-index of 0.67 is achieved compared to 0.72 in (V2). Multiple possibilities could have contributed to this discrepancy. First, the training of 3 different CNNs was not optimized to generate a well representative feature vector. This may have led to misleading feature vectors that make it hard to train a discriminative MTLR model. Second, the final aggregation of the output was the concatenating the three feature vectors. In an embodiment, more sophisticated aggregation of these feature vectors is introduced, such as an attention mechanism, in order to improve the representation power in the latent space.

Figure 9:
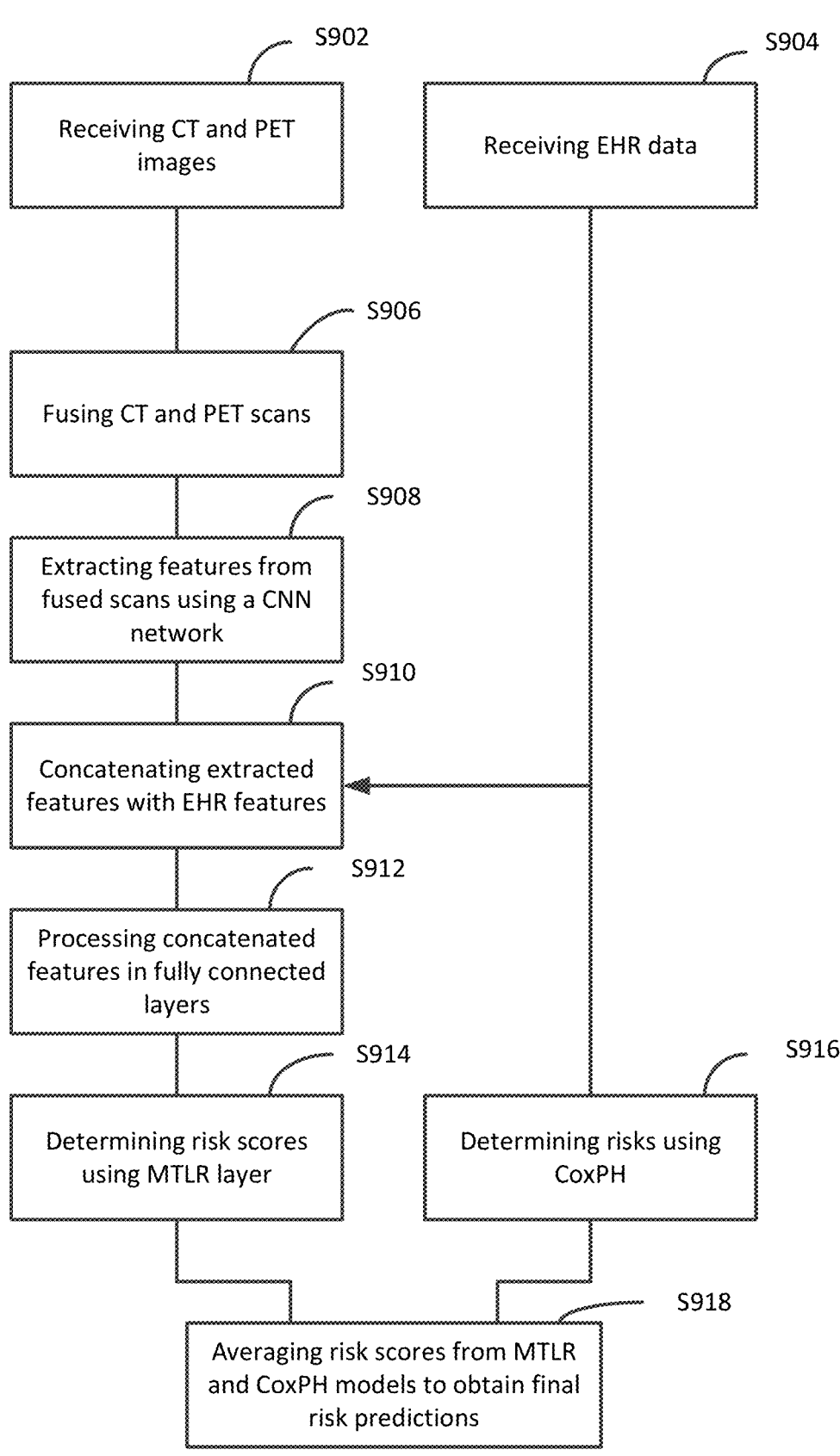
FIG. 9 is a flowchart for operation of the neural network architecture of FIG. 3.

FIG. 9 is a flowchart for operation of the neural network architecture of FIG. 3.

In V2 of the neural network architecture (FIG. 3), in steps S902, S904, inputs including CT images, PET images, and EHR data are received. In S906, a CT scan and a PET image scan are fused into a single image. In S908, features from the fused scan are extracted using a CNN 312. In S910, the extracted features are concatenated with EHR features. In S912, the concatenated features are processed in fully connected (FC) layers. In S914, the resulting features are used to determine risk scores in the MTLR. In addition, in S916, a CoxPH model 336 is used to determine risk scores using the EHR data. In S918, risk scores 322, 338 from MTLR 318 and CosPH 336 models are averaged to get the final risk predictions 342.

Next, a further embodiment is disclosed. As mentioned above, an embodiment of the disclosed invention shown in FIG. 3 achieved the top rank for Task 2 of the HECKTOR challenge, with a C-index of 0.72.

The inventors have observed that when oncologists estimate cancer patient survival, they rely on multimodal data. Even though some multimodal deep learning methods have been proposed, the majority rely on having two or more independent networks that share knowledge at a later stage in the overall model. On the other hand, oncologists do not do this in their analysis but rather initially fuse the information from multiple sources such as medical images and patient history.

Figure 10:
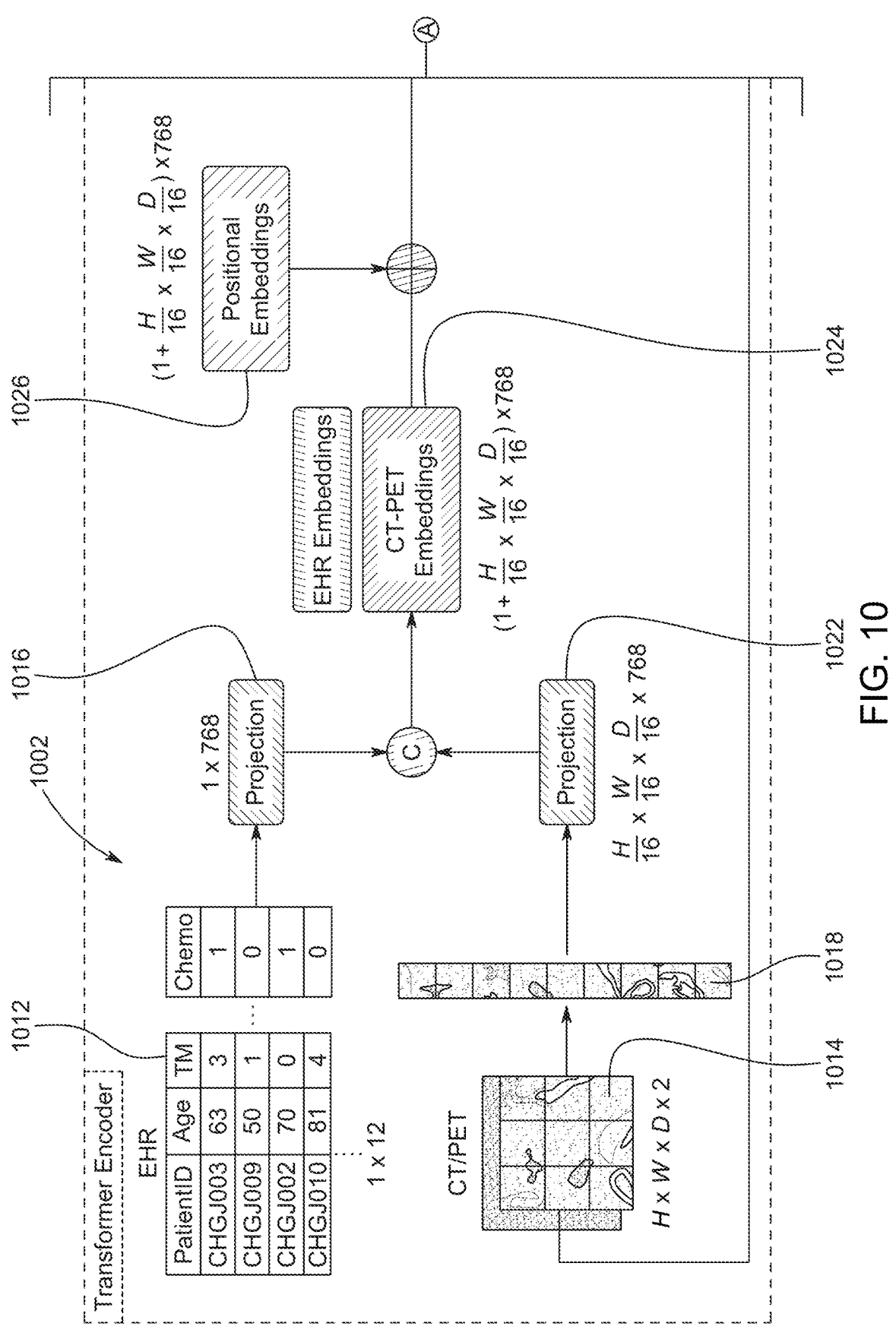
FIG. 10 is a block diagram of a TMSS architecture in accordance with an exemplary aspect of the disclosure.
Figure 10:
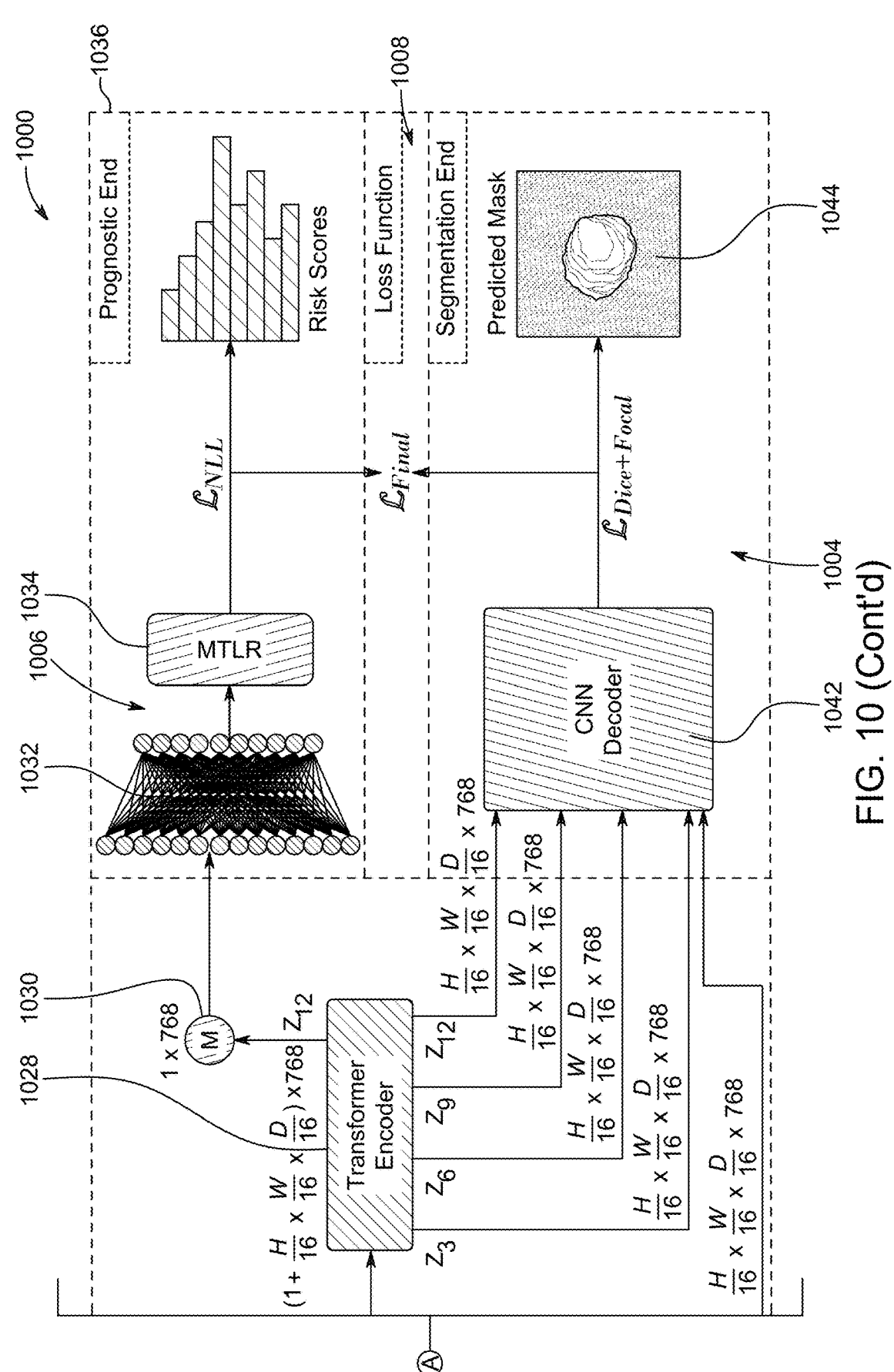
Figure 11A:
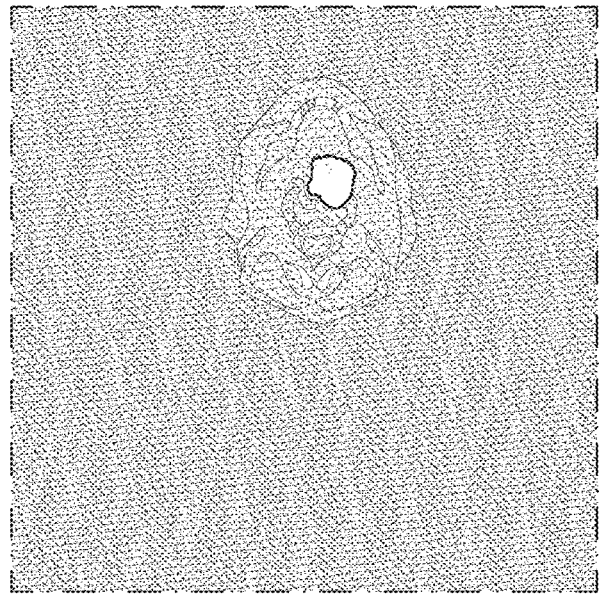
FIGS. 11A, 11B, 11C, 11D are example images of the training data set.
Figure 11B:
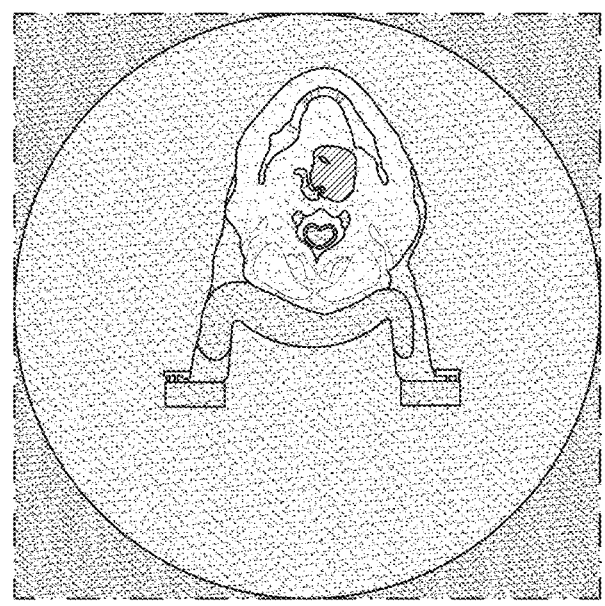
Figure 11C:
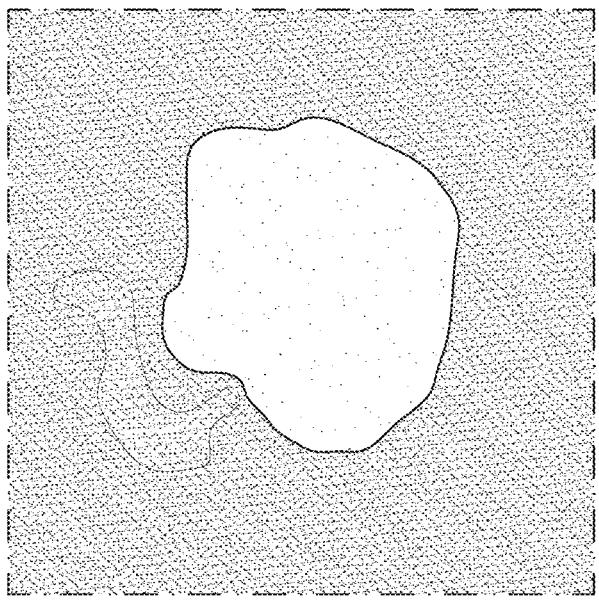
Figure 11D:
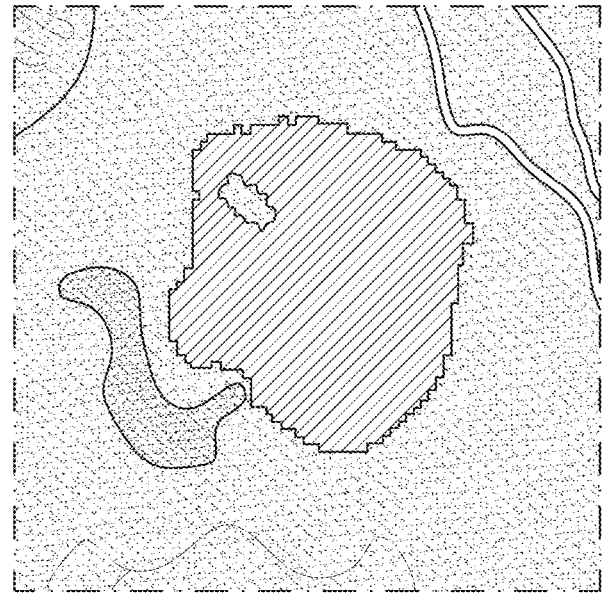

FIG. 10 is a block diagram of a TMSS architecture in accordance with an exemplary aspect of the disclosure. TMSS (Transformer based Multimodal network for Segmentation and Survival) is an end-to-end transformer for segmentation and survival prediction, in particular for segmentation and prognosis tasks on the training dataset from the HEad and neCK TumOR segmentation and outcome prediction in PET/CT images challenge (HECKTOR). The architecture includes a transformer-based encoder that is capable of attending to the available multimodal input data and the interaction between them. The architecture includes a combined loss function for segmentation mask and risk score predictions. The prognostic model significantly outperforms other methods with a concordance index of 0.763±0.14, thus achieving a higher C-index that even the neural network architecture of FIG. 3.

The architecture 1000 in FIG. 10 includes four main components: Transformer Encoder 1002, Segmentation End 1004, Prognostic End 1006, and Loss Function 1008.

Transformer Encoder 1002. In the TMSS architecture the encoder itself embeds both the CT/PET 1014 and EHR 1012 data and encodes positions 1026 for them accordingly while extracting dependencies (i.e. attention) between the different modalities. The 3D image with dimensions $x \in R^{H \times W \times D \times C}$ is reshaped into a sequence of flattened 2D patches $x_p \in R^{n*(P^3 C)}$, where H, W, and D are the height, width, and depth of the 3D image respectively, C denotes the number of channels, $P \times P \times P$ represents each patch's dimensions, and $n = HWD/P^3$ is the number of patches extracted. These patches are then projected 1022 to the embedding dimension h, forming a matrix $I \in R^{n \times h}$. Simultaneously, EHR data is also projected 1016 to a dimension $E \in R^{1 \times h}$. Both projections of images 1022 and EHR 1016 are concatenated, forming a matrix $X \in R^{(n+1) \times h}$ 1024. Positional encodings 1026 with the same dimension are added to each of the patches and the EHR projection as learnable parameters. The class token is dropped from the ViT as the solution does not address a classification task. See Dosovitskiy, A., Beyer, L., Kolesnikov, A., Weissenborn, D., Zhai, X., Unterthiner, T., Dehghani, M., Minderer, M., Heigold, G., Gelly, S., et al.: An image is worth 16×16 words: Transformers for image recognition at scale. arXiv preprint arXiv: 2010.11929 (2020), incorporated herein by reference in its entirety. The resulting embeddings 1024 are fed to a transformer encoder 1028 consisting of 12 layers, following the same pipeline as the original ViT, with normalization, multi-head attention, and multi-layer perceptron. The purpose of using self-attention is to learn relations between n+1 number of embeddings, including images and EHR. The self-attention inside the multi-head attention can be written as:

$$Z = \text{softmax}\left(\frac{QK^T}{\sqrt{D_q}}\right)V$$

Segmentation End 1004. The segmentation end 1004 is a CNN-based decoder 1042, similar to the decoder in Hatamizadeh, A., Tang, Y., Nath, V., Yang, D., Myronenko, A., Landman, B., Roth, H. R., Xu, D.: Unetr: Transformers for 3d medical image segmentation. In: Proceedings of the IEEE/CVF Winter Conference on Applications of Computer Vision. pp. 574-584 (2022), incorporated herein by reference in its entirety. The original images are fed to the decoder 1042 along with skip connections passed from ViT layers Z3, Z6, Z9, and Z12 (last layer). Only the image latent representations are passed through these skip connections $Z_r \in R^{(n) \times h}$ and fed to the CNN decoder 1042, where $E \in \{3, 6, 9, 12\}$. Convolution, deconvolution, batch normalization, and Rectified Linear Unit (ReLU) activation are used in the upsampling stage. See Saeed, N., Majzoub, R. A., Sobirov, I., Yaqub, M.: An ensemble approach for patient prognosis of head and neck tumor using multimodal data (2022), incorporated herein by reference in its entirety. The segmentation end 1004 produces a prediction mask 1044

Prognostic End 1006. The prognostic path 1006 receives the output of the encoder 1028 with dimensions $Z_{12} \in R^{(n+1) \times h}$, and its mean value is computed, reducing the dimensions down to $Z_{mean} \in R^{1 \times h}$. This latent vector is then forwarded to two fully connected layers 1032, reducing the dimensions from h to 512 and 128 respectively. The resulting feature map is then fed to an MTLR model 1034 for final risk prediction. The MTLR module 1034 divides the future horizon into different time bins, set as a hyperparameter, and for each time bin a logistic regression model 1036 is used to predict if an event occurs or not.

Loss Function 1008. Since the network performs two tasks concurrently, a combination of three losses is formulated as the final objective function. The segmentation end 1004 is supported by the sum of a dice loss, $\mathcal{L}_{ice}$, and a focal loss $\mathcal{L}_{Focal}$, where N is the sample size, $\hat{p}$ is the model prediction, y is the ground truth, $\alpha$ is the weightage for the trade-off between precision and recall in the focal loss (set to 1), and $\gamma$ is focusing parameter (empirically set to 2).

$$\mathcal{L}_{Dice} = \frac{2 \sum_i^N \hat{p}_i y_i}{\sum_i^N \hat{p}_i^2 + \sum_i^N y_i^2},$$

$$\mathcal{L}_{Focal} = -\sum_i^N \alpha y_i (1 - \hat{p}_i)^\gamma \log(\hat{p}_i) - (1 - y_i)\hat{p}_i^{\ \gamma} \log(1 - \hat{p}_i),$$

The prognostic end 1006 has a negative-log likelihood loss (NLL) as given in $\mathcal{L}_{NLL}$. Here, the first line in the NLL loss corresponds to uncensored data, the second line corresponds to censored data and the third line is the normalizing constant. See Kazmierski, M.: Machine Learning for Prognostic Modeling in Head and Neck Cancer Using Multimodal Data. Ph.D. thesis, University of Toronto (Canada) (2021), incorporated herein by reference in its entirety. The product $$w_k^T x^{(n)}$$

is the model prediction, $b_k$ is the bias term, and $y_k$ is the ground truth.

$$\mathcal{L}_{NLL}(\theta, D) = \sum_{n:\delta^{(n)}=1} \sum_{k=1}^{K-1} \left(w_k^T x^{(n)} + b_k\right)y_k^{(n)} +$$

$$\sum_{n:\delta^{(n)}=0} \log\left(\sum_{k=1}^{K-1} \mathbb{1}\{t_i \geq T^{(n)}\}\exp\left(\sum_{k=1}^{K-1}\left((w_k^T x^{(n)} + b_k)y_k^{(n)}\right)\right)\right) -$$

$$\sum_{n=1}^{N} \log\left(\sum_{i=1}^{K-1}\exp\left(\sum_{k=1}^{K-1}w_k^T x^{(n)} + b_k\right)\right),$$

The final loss 1008 used for network training is $\mathcal{L}_{Final}$ as a combination of the three losses. The hyperparameter $\beta$, provides weightage to either side of the model paths, and is empirically set to 0.3.

$$\mathcal{L}_{Final} = \beta * (\mathcal{L}_{Dice} + \mathcal{L}_{Focal}) + (1-\beta) * \mathcal{L}_{NLL}.$$

An experimental setup was created as an example implementation. An imaging dataset was provided for training. A multicentric dataset of PET and CT images, their segmentation masks, and electronic health records are available on the HECKTOR challenge platform.

FIG. 11 illustrates a sample from the imaging dataset. FIG. 11A depicts the original PET scan. FIG. 11B depicts the original CT scan and the imposed ground truth mask. FIG. 11C shows the 80×80×48 cropped PET and FIG. 11D shows the 80×80×48 cropped CT with ground truth mask.

The data comes from six different clinical centers; 224 and 101 patient records for training and testing respectively. The testing set ground truths, both for segmentation and prognosis tasks are hidden for competition purposes, thus are preferably not used to validate the method of the present disclosure. Therefore, k-fold (where k==5) cross validation was performed on the training set. EHR is comprised of data pertinent to gender, weight, age, tumor stage, tobacco and alcohol consumption, chemotherapy experience, human papillomavirus (HPV), and other data. Imaging data contains CT, PET, and segmentation masks for tumor; sample slices are illustrated in FIG. 11A to 11D, respectively.

Data Preprocessing is performed. Both the CT and PET images are resampled to an isotropic voxel spacing of 1.0 $mm^3$. Their intensity values are then normalized before being fed to the network. Furthermore, as in Saeed et al. the images are cropped down to 80×80×48 $mm^3$ as in for two main purposes; the first is to fairly compare the results to the state-of-the-art in, which also used images with these dimensions. The second is that this reduction of image dimensions, in turn, speeds up training and inference processes and allows to run multiple experiments.

EHR, being multicentric, is missing some data, such as tobacco and alcohol consumption, from most of the centers; therefore, they were dropped. 75% of the total data is censored, assumed to have stopped the follow-up to the hospitals.

The neural network model was implemented for a single NVIDIA RTX A6000 (48 GB). The PyTorch library was used to implement the network and train the model for 50 epochs. The batch size was set to 16, the learning rate to 4$e$-3, and the weight decay to 1e−5. The step decay learning rate strategy was used to reduce the learning rate by a factor of 10 after the 35 epochs.

The scans are patched into the size of 16×16×16, and projected to the embedding dimension of 768. The total number of layers used in the encoder was 12, each having 12 attention heads.

The β in the loss function was set to 0.3. All the hyperparameters were chosen empirically, using the framework OPTUNA. See Akiba, T., Sano, S., Yanase, T., Ohta, T., Koyama, M.: Optuna: A next-generation hyperparameter optimization framework. CoRR abs/1907.10902 (2019), incorporated herein by reference in its entirety. The evaluation metrics for the prognosis risk was concordance index (C-index), and for the segmentation was dice similarity coefficient (DSC).

Figure 12A:
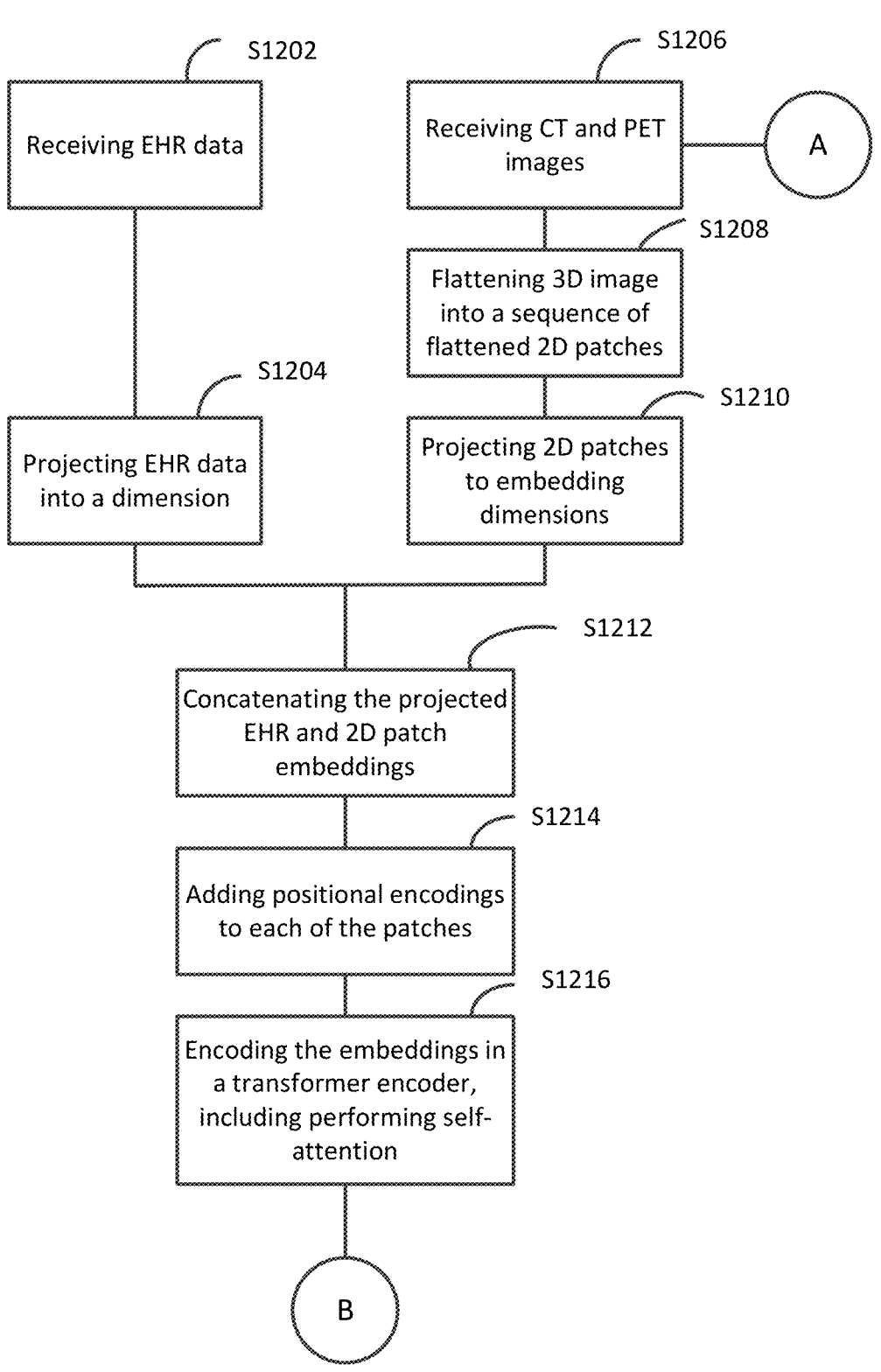
FIGS. 12A, 12B is a flowchart for operation of the neural network architecture of FIG. 10.
Figure 12B:
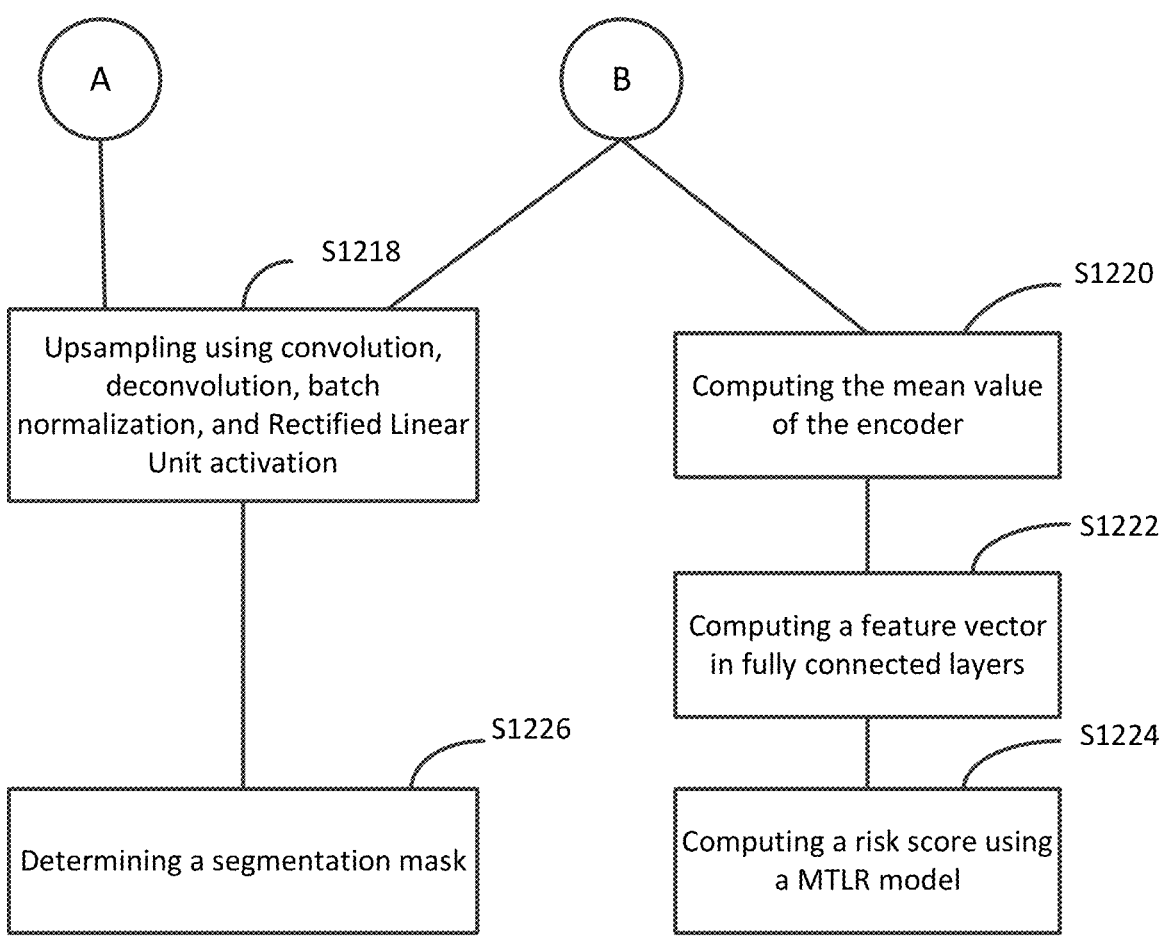

FIGS. 12A, 12B is a flowchart for operation of the neural network architecture of FIG. 10.

In S1202, the EHR data is input, while in S1206, CT scans and PET scans are input. in S1208, the 3D image from the CT and PET scans with dimensions $x \in R^{H \times W \times D \times C}$ is reshaped into a sequence of flattened 2D patches $x_p \in R^{n \times (^3 C)}$, where H, W, and D are the height, width, and depth of the 3D image respectively, C denotes the number of channels, P×P×P represents each patch's dimensions, and $n=HWD/P^3$ is the number of patches extracted. In S1210, these patches are then projected 1022 to the embedding dimension h, forming a matrix $I \in R^{n \times h}$. Simultaneously, in S1204, EHR data is also projected 1016 to a dimension $E \in R^{1 \times h}$. In S1212, both projections of images 1022 and EHR 1016 are concatenated, forming a matrix $X \in R^{(n+1) \times h}$ 1024. In S1214, positional encodings 1026 with the same dimension are added to each of the patches and the EHR projection as learnable parameters.

In S1216, the resulting embeddings 1024 are fed to a transformer encoder 1028, including normalization, multi-head attention, and multi-layer perceptron.

In S1218, in a segmentation component 1004, convolution, deconvolution, batch normalization and Rectified Linear Unit activation are used in an upsampling stage.

In a prognostic component 1006, in S1220, the mean of the transformer encoder 1028 is determined. In S1222, the resultant vector is then forwarded to two fully connected layers 1032, reducing the dimensions from h to 512 and 128 respectively. In S1224, a risk score is computed using a MTLR model 1034. In S1226, a segmentation mask is output from CNN decoder 1042.

Figure 13:
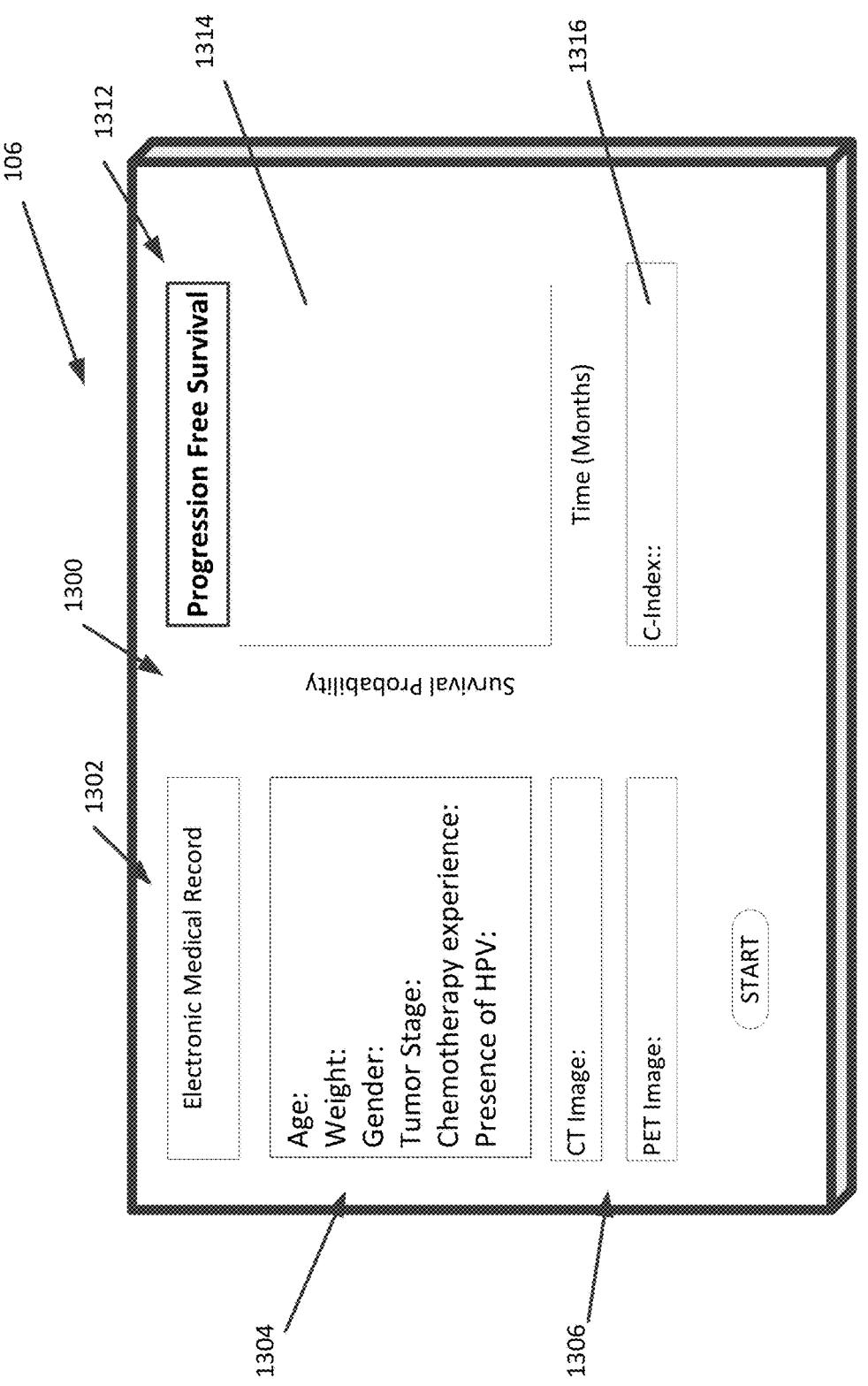
FIG. 13 is an example user interface for inference for a patient in accordance with an exemplary aspect of the disclosure.

In an exemplary implementation, the neural network model for segmentation and survival prediction may be executed in a computer device 106. FIG. 13 is an example user interface for inference for a patient in accordance with an exemplary aspect of the disclosure. A display 1300 for the computer device 106 can display input features for a patient 1302 and an output for prognosis 1312. The patient input features include patient information obtained from the patient's electronic health record (EHR) 1304 and image files obtained from scans, computed tomography (CT) and positron emission tomography (PET) 1306. The output may include a graph 1314 of progression free survival, survival probability and time (in months, days, years). In an exemplary embodiment, the output may include one or more measures of performance of the prognosis model, for example the concordance index (C-index) 1316.

In one embodiment, when the final risk score is below a predetermined threshold, indicating that the prognosis is no head or neck tumor, the display 1300, or some other display device, may include a simple indication of no cancer, without other output information. For example, an indication may include an LED indicator light on a scan device 102 itself. Other alternatives may include a sound, a blinking light, and entry into an electronic health record of the patient.

Results of the experimental setup are discussed next. The HECKTOR dataset was used as described above for the diagnosis and prognosis of patients with head and neck cancer. Several experiments were conducted, all in 5-fold cross validation using the training dataset from the challenge. All the experiments were trained and cross validated using the same settings.

The following Table shows prognosis performance by different models on the HECKTOR dataset. Data reported are the mean and standard deviation for 5-fold cross validation.

|  | CoxPH | MTLR | Deep MTLR | Ensemble | TMSS |
|---|---|---|---|---|---|
| C-index | 0.682 ± 0.06 | 0.600 ± 0.031 | 0.692 ± 0.06 | 0.704 ± 0.07 | 0.763 ± 0.14 |

The Table shows the results of all conducted experiments. Experiments started with the commonly used algorithms for survival analysis. CoxPH, MTLR and Deep MTLR were applied as baselines. As is vivid, CoxPH, achieving C-index of 0.68, outperforms the MTLR model by a huge degree of 0.08, yet introducing neural nets to MTLR (i.e. Deep MTLR) boosted the score to 0.692. All three calculate the risk using only the EHR data on account of their architectural nature. As in Saeed et al. an ensemble of CNNs for the images with MTLR, and CoxPH for EHR achieved the highest C-index on the testing set which was also implemented to train and validate using the same fashion as the original work. The ensemble was able to reach C-index of 0.704. Finally, the TMSS model, embedding EHR information in the input and using transformers which is unlike the ensemble, outperforms all the other models, achieving a mean C-index of 0.763.

For segmentation comparison purposes UNETR was implemented, a segmentation standalone network using the same settings as. See Sobirov, I., Nazarov, O., Alasmawi, H., Yaqub, M.: Automatic segmentation of head and neck tumor: How powerful transformers are? arXiv preprint arXiv: 2201.06251 (2022), incorporated herein by reference in its entirety. The model achieved DSC of $0.772\pm0.03$, which was only 0.002 lower than that of UNETR network optimized for segmentation which achieved DSC of $0.774\pm0.01$.

The following is a discussion of the results of the experiments. The traditional approach to automate diagnosis and prognosis of cancerous patients is generally performed in two stages; either, as in Kazmierski, a standalone network that extracts tumor radiomics such as tumor volume and feeds it to a prognostic model, or as in SOTA, Saeed et al., that uses an ensemble of CNNs (see FIG. 3, above) to extract features and concatenate with the EHR, then feeds them to another network for the risk prediction.

However, TMSS approach tackles both problems at once, in an end-to-end net-work, making it simpler and easier to train. The TMSS approach outperforms other models by a good margin using vision transformers. Encoding EHR data into the network was newly introduced to mimic the way doctors review patient data. This has effectively boosted the accuracy of prognosis as shown in the above Table. The aforementioned results show the superiority of transformers in handling multimodal data. It may be hypothesized that the attention embedded in the transformer blocks, along with their ability to accommodate multimodal data, allows them to find relations across the modalities and within their intermediate representations. That can help them better address the tasks at hand. The use of multiple losses boosts the ability of the model to better interpolate within the given data, and hopefully become more robust when subjected to unseen ones. The introduction of the weighting variable β with a value of 0.3 penalizes the model more for prognosis errors coercing it to learn the features better and adjust its weights accordingly for an accurate prognosis.

Although the main goal of the TMSS model is prognosis, comparable results are achieved with UNETR which was optimized for segmentation. This reinforces the hypothesis that both tasks compliment and aid each other for a better performance. It also sheds light on how improving the segmentation task in turn hones the prognosis results and helps the model learn better representation of both images and EHR data.

Numerous modifications and variations of the present invention are possible in light of the above teachings. It is therefore to be understood that within the scope of the appended claims, the invention may be practiced otherwise than as specifically described herein.

For example, embodiments may include self-supervised learning and pretraining of the network. They have proven to help models learn better, especially when the data is limited. Additionally, the current network can be applied on similar tasks with different datasets.

The invention claimed is:

1. A system for prognosis of head and neck cancer, comprising:
processing circuitry configured to
project clinical data of a patient into a first feature vector,
project three-dimensional (3D) multimodal images of a head and neck area of the patient into a second feature vector, including:
flattening the 3D multimodal images into a sequence of flattened two-dimensional (2D) patches, and
projecting the flattened 2D patches into the second feature vector,
generate a third feature vector based on the first feature vector and the second feature vector by:
concatenating the first feature vector and the second feature vector into a concatenated feature vector, and
generating the third feature vector based on positional encoding being added to the concatenated feature vector,
encode the third feature vector using a transformer-based encoder that encodes the third feature vector based on a self-attention mechanism, and
calculate a risk score of prognosis of head and neck cancer for the patient based on the encoded third feature vector.

2. The system of claim 1, wherein the processing circuitry is configured to calculate the risk score by
calculating a mean value of the encoded third feature vector,
generating a fourth feature vector based on the mean value being input into fully connected layers, and
calculating the risk score based on the fourth feature vector being input into a multi-task logistic regression (MTLR) model.

3. The system of claim 2, wherein the MTLR model includes a series of logistic regression models built on different time intervals, and a non-linear transformation neural network.

4. The system of claim 2, wherein the processing circuitry is further configured to generate a segmentation mask based on the multimodal images being input into a convolutional neural network (CNN)-based decoder along with skip connections passed from the transformer-based encoder.

5. The system of claim 4, wherein the transformer-based encoder includes twelve layers and the skip connections are passed from the third layer, the sixth layer, the ninth layer, and the twelve layer of the transformer-based encoder.

6. The system of claim 4, wherein the processing circuitry is further configured to calculate a loss function based on a weighted sum of a first loss for generating the segmentation mask and a second loss for calculating the risk score, and wherein the first loss is a sum of a dice loss and a focal loss and the second loss is a negative-log likelihood loss.

7. The system of claim 1, wherein the processing circuitry is further configured to determine a surgery or treatment plan based on the risk score of the prognosis of head and neck cancer of the patient.

8. The system of claim 1, wherein the clinical data includes electronic health records of the patient and the multimodal images include computed tomography (CT) and positron emission tomography (PET) scans of the patient.

9. A method for prognosis of head and neck cancer, comprising:

projecting clinical data of a patient into a first feature vector;

projecting three-dimensional (3D) multimodal images of a head and neck area of the patient into a second feature vector, including:

flattening the 3D multimodal images into a sequence of flattened two-dimensional (2D) patches; and projecting the flattened 2D patches into the second feature vector:

generating a third feature vector based on the first feature vector and the second feature vector by:

concatenating the first feature vector and the second feature vector into a concatenated feature vector; and generating the third feature vector based on positional encoding being added to the concatenated feature vector:

encoding the third feature vector using a transformer-based encoder that encodes the third feature vector based on a self-attention mechanism; and calculating a risk score of prognosis of head and neck cancer for the patient based on the encoded third feature vector.

10. The method of claim 9, wherein the clinical data includes electronic health records of the patient and the multimodal images include computed tomography (CT) and positron emission tomography (PET) scans of the patient.

11. The method of claim 9, wherein the calculating the risk score includes:

calculating a mean value of the encoded third feature vector;

generating a fourth feature vector based on the mean value being input into fully connected layers; and calculating the risk score based on the fourth feature vector being input into a multi-task logistic regression (MTLR) model.

12. The method of claim 11, wherein the MTLR model includes a series of logistic regression models built on different time intervals, and a non-linear transformation neural network.

13. The method of claim 11, further comprising generate a segmentation mask based on the multimodal images being input into a convolutional neural network (CNN)-based decoder along with skip connections passed from the transformer-based encoder.

14. The method of claim 13, wherein the transformer-based encoder includes twelve layers and the skip connections are passed from the third layer, the sixth layer, the ninth layer, and the twelve layer of the transformer-based encoder.

15. The method of claim 13, further comprising calculating a loss function based on a weighted sum of a first loss for generating the segmentation mask and a second loss for calculating the risk score, wherein the first loss is a sum of a dice loss and a focal loss and the second loss is a negative-log likelihood loss.

* * * * *